(12) United States Patent
Saito et al.

(10) Patent No.: US 11,472,784 B2
(45) Date of Patent: *Oct. 18, 2022

(54) GRISEOFULVIN COMPOUND

(71) Applicant: Daiichi Sankyo Company, Limited, Tokyo (JP)

(72) Inventors: Keiji Saito, Atsugi (JP); Katsuyoshi Nakajima, Shinagawa-ku (JP); Toru Taniguchi, Bunkyo-ku (JP); Osamu Iwamoto, Yokohama (JP); Satoshi Shibuya, Kawasaki (JP); Yasuyuki Ogawa, Yokosuka (JP); Kazumasa Aoki, Koto-ku (JP); Nobuya Kurikawa, Shinagawa-ku (JP); Shinji Tanaka, Edogawa-ku (JP); Momoko Ogitani, Ota-ku (JP); Eriko Kioi, Yokohama (JP); Kaori Ito, Koto-ku (JP); Natsumi Nishihama, Yokohama (JP); Tsuyoshi Mikkaichi, Saitama (JP); Wataru Saitoh, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/212,373

(22) Filed: Mar. 25, 2021

(65) Prior Publication Data
US 2021/0292292 A1  Sep. 23, 2021

Related U.S. Application Data

(63) Continuation of application No. 16/844,621, filed on Apr. 9, 2020, now Pat. No. 10,975,052, which is a continuation of application No. 16/561,459, filed on Sep. 5, 2019, now Pat. No. 10,654,821, which is a continuation of application No. 16/088,696, filed as
(Continued)

(30) Foreign Application Priority Data

Mar. 30, 2016 (JP) .................. 2016-067076

(51) Int. Cl.
| | | |
|---|---|---|
| C07D 307/94 | (2006.01) | |
| C07D 405/04 | (2006.01) | |
| C07D 405/10 | (2006.01) | |
| C07D 407/12 | (2006.01) | |
| C07D 413/04 | (2006.01) | |
| C07D 413/10 | (2006.01) | |
| C07D 413/14 | (2006.01) | |
| A61K 31/343 | (2006.01) | |
| A61K 31/4155 | (2006.01) | |
| A61K 31/4245 | (2006.01) | |

(52) U.S. Cl.
CPC .......... C07D 307/94 (2013.01); A61K 31/343 (2013.01); A61K 31/4155 (2013.01); A61K 31/4245 (2013.01); C07D 405/04 (2013.01); C07D 405/10 (2013.01); C07D 407/12 (2013.01); C07D 413/04 (2013.01); C07D 413/10 (2013.01); C07D 413/14 (2013.01)

(58) Field of Classification Search
CPC .. C07D 307/94; C07D 405/04; C07D 405/10; C07D 407/12; C07D 4013/04; C07D 4013/10; C07D 4013/14; A61K 31/343; A61K 31/4155; A61K 31/4245
See application file for complete search history.

(56) References Cited

U.S. PATENT DOCUMENTS

| | | | |
|---|---|---|---|
| 10,570,109 B2 * | 2/2020 | Saito | ................. A61K 31/4155 |
| 10,654,821 B2 * | 5/2020 | Saito | ................. A61K 31/4245 |
| 10,975,052 B2 * | 4/2021 | Saito | ................. A61K 31/4155 |

(Continued)

FOREIGN PATENT DOCUMENTS

| | | |
|---|---|---|
| CN | 104860909 A | 8/2015 |
| DE | 4430910 A1 | 3/1996 |

(Continued)

OTHER PUBLICATIONS

"U.S. Appl. No. 16/648,570; office action dated Aug. 13, 2021".
(Continued)

Primary Examiner — Timothy R Rozof
(74) Attorney, Agent, or Firm — Myers Bigel, P.A.

(57) ABSTRACT

An object of the present invention is to provide a compound having an anti-inflammatory activity or a pharmacologically acceptable salt thereof.

The solution of the present invention is a compound of general formula (1) or a pharmacologically acceptable salt thereof.

[Formula 1]

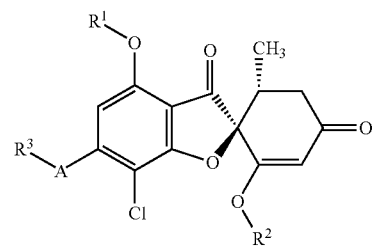

(1)

wherein the symbols in the formula are defined below: $R^1$: e.g., a C1-C6 alkyl group; $R^2$: a C1-C6 alkyl group; A: e.g., an oxygen atom; and $R^3$: e.g., a C1-C6 alkyl group.

13 Claims, No Drawings

Related U.S. Application Data application No. PCT/JP2017/012777 on Mar. 29, 2017, now Pat. No. 10,570,109.

(56) References Cited

U.S. PATENT DOCUMENTS

| | | | |
|---|---|---|---|
| 2015/0191443 | A1 | 7/2015 | Marion et al. |
| 2020/0216433 | A1 | 7/2020 | Saito et al. |
| 2020/0239425 | A1 | 7/2020 | Saito et al. |

FOREIGN PATENT DOCUMENTS

| | | |
|---|---|---|
| JP | H03255081 A | 11/1991 |
| TW | 201738222 A | 11/2017 |
| WO | 2009000937 A1 | 12/2008 |
| WO | 2010072770 A2 | 7/2010 |
| WO | 2010124695 A1 | 11/2010 |
| WO | 2017170623 A1 | 10/2017 |
| WO | 2019065928 A1 | 4/2019 |

OTHER PUBLICATIONS

"Extended European Search Report corresponding to European Application No. 18860748.5 dated May 10, 2021".
"Office Action corresponding to Brazilian Application No. 11 2018 069712 5 dated Apr. 15, 2021".
D'Arcy, P.F , et al., "The Anti-Flammatory Action of Griseofulvin in Experimental Animals", Pharmaceutical and Clinical Research 12(1):659-665 (Sep. 1, 1960.
"U.S. Appl. No. 16/561,459; office action dated Sep. 27, 2019".
"U.S. Appl. No. 16/844,621; office action dated May 15, 2020".
"U.S. Appl. No. 16/844,621; office action dated Aug. 18, 2020".
"Extended European Search Report corresponding to European Application No. 17775160.9 dated Sep. 20, 2019".
"International Preliminary Report on Patentability corresponding International Application No. PCT/JP2017/012777 dated Oct. 11, 2018".
"International Preliminary Report on Patentability corresponding to International Application No. PCT/JP2018/036160 dated Apr. 9, 2020".
"International Search Report and Written Opinion corresponding to International Application No. PCT/JP2018/036160 dated Dec. 11, 2018".
"International Search Report and Written Opinion dated Jun. 6, 2017, issued in corresponding International Application No. PCT/JP2017/012777, filed Mar. 29, 2017, 9 pages."
"Office Action corresponding to Australian Application No. 2017244777 dated Jul. 6, 2020".
"Office Action corresponding to Canadian Application No. 3,018,316 dated Oct. 1, 2019".
"Office Action corresponding to Colombian Patent Application No. NC2018/0010787 dated May 7, 2020".
"Office Action corresponding to Indian Application No. 201817039908 dated Oct. 25, 2019".
"Office Action corresponding to Indonesian Application No. P-00201807645 dated Dec. 10, 2020".
"Office Action corresponding to Israeli Application No. 262,020 dated Jun. 22, 2020".
"Office Action corresponding to Japanese Application No. 2018-508114 dated Oct. 21, 2020".
"Office Action corresponding to Russian Application No. 2018137851 dated Apr. 17, 2020".
"Office Action corresponding to Taiwanese Application No. 106110433 dated Dec. 24, 2020".
Arkley, V., , et al., ", "Griseofulvin Analogues. Part I: Modification of the Aromatic Ring," Journal of the Chemical Society 241:1260-1268, Apr. 1962."
Asahina , et al., ""Griseofulvin has a potential to modulate the expression of cell adhesion molecules on leukocytes and vascular endothelial cells", International Immunopharmacology 1(1):75-83 (2001)".
Cohen, A., , et al., ", "Treatment of Shoulder-Hand Syndrome With Griseofulvin," Journal of the American Medical Association 173(5):542-543, Jun. 1960."
Gentles, J.C , "Experimental Ringworm in Guinea Pigs: Oral Treatment With Griseofulvin", Nature 182:476-477, Aug. 1958.
Goodall, S.R., , et al., ", "Griseofulvin Analogues. Part VII: Replacements in the Aromatic Ring," Journal of the Chemical Society 302:1610-1619, Mar. 1963."
Green, G. F. H. , et al., "22. Griseofulvin Analogues. Part IX. Proton Magnetic Resonance Studies., Journal of the Chemical Society, 1964, pp. 144-148".
Ho, Y.-S., , et al., ", "Griseofulvin Potentiates Antitumorigenesis Effects of Nocodazole Through Induction of Apoptosis and G2/M Cell Cycle Arrest in Human Colorectal Cancer Cells," International Journal of Cancer 91(3):393-401, Feb. 2001."
Kraft, R. , et al., ", A cell-based fascin bioassay identifies compounds with potential anti -metastasis or cognition-enhancing functions, Disease Models & Mechanisms, 2013, 6(1), pp. 217-235".
Oxford, A.E., , et al., ", "XXIX. Studies In the Biochemistry of Micro-Organisms. LX. Griseofulvin, C17H17O6C1, A Metabolic Product of Penicillium griseo-fulvum Dierckxx," Biochemical Journal 33(2):240-248, Feb. 1939."
Petersen, A.B., , et al., ", "The Chemistry of Griseofulvin," Chemical Reviews 114(24):12088-12107, Dec. 2014."
Rodriguez, J. A. , et al., ", The effects of some porphyrinogenic drugs on the brain cholinergic system, Cellular and Molecular Biology, 2002, 48 (1), pp. 103-110".
Sehgal , et al., ""Antifungal Agents: Unapproved Uses, Dosages, or Indications", Clinics in Dermatology 20:481-489 (2002)".
Sehgal, V.N., , et al., ", "Histopathological Evaluation of Griseofulvin Therapy in Lichen planus," Dermatologica 161 (1):22-27, 1980."
Sorrentino, L., , et al., ", "Anti-inflammatory Properties of Griseofulvin," Agents and Actions 7(1):157-162, Mar. 1977."
Tamaki, K., , et al., ", "Successful Treatment of Pigmented Purpuric Dermatosis With Griseofulvin," British Journal of Dematology 132(1):159-160, Jan. 1995."
Tamaki, K., , et al., ", "Treatment of Plasma Cell Cheilitis With Griseofulvin," Journal of the American Academy of Dermatology 30(5, Pt 1):789-790, May 1994."
Vincent, A. M. , et al., ", Identification of candidate drugs for the treatment of ALS, Amyotrophic Lateral Sclerosis and Other Motor Neuron Disorders, 2005, 6(1), pp. 29-36".
Wehland, J., , et al., ", "Interaction of Griseofulvin With Microtubules, Microtubule Protein and Tubulin," Journal of Molecular Biology 111(3):329-342, Apr. 1977."
Williams, D.I., , et al., ", "Oral Treatment of Ringworm With Griseofulvin," The Lancet 2(7058):1212-1213, Dec. 1958."
"Office Action corresponding to Chinese Application No. 201780017933.3 dated Sep. 18, 2021".
"Office Action corresponding to Indian Application No. 202017016710 dated Nov. 16, 2021".
"Office Action corresponding to Korean Application No. 10-2018-7027758 dated Jan. 20, 2022".
"Office Action corresponding to Philippine Application No. 1-2018-502012 dated Feb. 10, 2022".
"Office Action corresponding to Russian Application No. 2020114910 dated Nov. 24, 2021".
Belikov, V. G, "Relationships between the Chemical Structure, Properties of the Compound, and Its Effect on a Living Body", Pharmaceutical Chemistry Chapter 2.6:27-29 (2017).
Kovaleva, M. A, et al., "Forced Swim Test in Preclinical Studies", International bulletin of veterinary medicine No. 4:90-95 (2015).
Kümmerer, Klaus , "Pharmaceuticals in the environment", Annual Review of Environment and Resources 35:57-75 (Aug. 18, 2010).
"Office Action corresponding to Israeli Application No. 273,339 dated Apr. 3, 2022".
"Office Action corresponding to Japanese Application No. 2019-545656 dated Mar. 4, 2022".
"Written Opinion corresponding to Singapore Application No. 11202002973W dated Aug. 31, 2021".
"Extended European Search Report corresponding to European Application No. 21212977.9 dated Jun. 3, 2022".

(56) References Cited

OTHER PUBLICATIONS

"Office Action corresponding to Mexican Application No. MX/a/2020/003383 dated May 13, 2022".
"Examination Report corresponding to Australian Application No. 2018342423 dated Apr. 1, 2022".
"Office Action corresponding to Taiwanese Application No. 107133866 dated Aug. 2, 2022".
Office Action corresponding to Brazilian Application No. 1120200062391 dated Aug. 16, 2022.

* cited by examiner

GRISEOFULVIN COMPOUND

CROSS-REFERENCE TO RELATED APPLICATIONS

This application is a continuation of and claims priority to U.S. patent application Ser. No. 16/844,621, filed Apr. 9, 2020, now U.S. Pat. No. 10,975,052, which is a continuation of and claims priority to U.S. patent application Ser. No. 16/561,459, filed Sep. 5, 2019, now U.S. Pat. No. 10,654,821, which is a continuation of and claims priority to U.S. patent application Ser. No. 16/088,696, filed Sep. 26, 2018, now U.S. Pat. No. 10,570,109, which is a § 371 national phase application of PCT Application No. PCT/JP2017/012777 filed Mar. 29, 2017, which claims priority to Japanese Application No. 2016-067076 filed Mar. 30, 2016, the entire contents of each of which is incorporated by reference herein.

TECHNICAL FIELD

The present invention relates to a compound having a specific chemical structure having an anti-inflammatory activity or a pharmacologically acceptable salt thereof.

BACKGROUND ART

Griseofulvin is an antibiotic substance isolated for the first time by AE Oxford et al, from one of *Penicillium* belonging to *Aspergillus oryzae*, i.e., *penicillium griseofulvum* (Non patent Reference 1) in 1939. Griseofulvin is mainly administered orally. However, it is a less soluble and readily absorbable medicinal substance and thus complicated in its oral absorption kinetics. Griseofulvin is used as an antifungal drug against dermatophytes such as Microsporum, Trichophyton and Epidermophyton (Non patent References 2, 3).

Griseofulvin binds to tubulin within a cell to thereby terminate the cell cycle at the G2/M period and induce abnormality in mitotic division, with the result that growth of various cells of, e.g., fungi, plants and mammals is suppressed. Compared to mammalian cells, fungal cells are suppressed in growth at an extremely low concentration of griseofulvin. This is considered to be because the binding affinity of griseofulvin for fungus tubulin is higher than for mammalian tubulin. Griseofulvin also binds to microtubule-associated proteins (MAPS) to suppress dynamic instability of microtubules, thereby stabilizing microtubule movement (Non patent Reference 4).

Griseofuivin has a growth suppression action on human cancer cells and an activity which induces apoptosis thereof. Griseofulvin, if it is applied to a tumor transplanted in an athymic nude mouse in combination with nocodazole, exhibits antitumor activity. From this, griseofulvin is expected to have effectiveness as an anti-cancer agent (Non patent Reference 5).

In the meantime, it has long been known that griseofulvin has an anti-inflammatory activity other than the anti-fungal action. For example, it was found that griseofulvin exhibits anti-inflammatory activity on rat inflammation models with formalin edema and cotton pellet granuloma (Non patent Reference 6). In clinical practice, it is reported that griseofulvin has a medicinal effect on nonfungal inflammatory skin diseases such as lichen planus (Non patent Reference 7), plasma cell cheilitis (Non patent Reference 8) and pigmented purpuric dermatosis (Non patent Reference 9).

It is also reported that griseofulvin has a medicinal effect on, e.g., livedoid vasculitis (Non patent Reference 9), polyarthritis such as shoulder-hand syndrome and scapulo-humeral periarthritis (Non patent References 6, 10).

It is found that griseofulvin has as action on the microtubules of leucocytes and an antagonistic action, in vitro, on chemical mediators of inflammation such as histamine, serotonin and prostaglandin (Non patent Reference 6). However, the specific mechanism of griseofulvin action in anti-inflammation has not yet been elucidated.

Likewise, griseofulvin has various physiological activities and, until now, various derivatives of griseofulvin have been synthesized through replacement of substituents (Non patent Reference 11).

CITATION LIST

Non Patent References

Non patent Reference 1: Oxford A E, Raistrick H, Simonart P. Studies in the biochemistry of micro-organisms: Griseofulvin, C(17)H (17)O (6)Cl, a metabolic product of *Penicillium* uriseo-fulvum Dierckx. Biochem J. 1939 February; 33 (2): 240-8

Non patent Reference 2: Gentles J C. Experimental ringworm in guinea pigs: oral treatment with griseofulvin. Nature. 1958 Aug. 16; 182 (4633): 476-7

Non patent Reference 3: Williams D I, Marten R H, Sarkany I. Oral treatment of ringworm with griseofulvin. Lancet. 1958 Dec. 6; 2 (7058): 1212-3

Non patent Reference 4: Wehland J, Herzog W, Weber K. Interaction of griseofulvin with microtubules, microtubule protein and tubulin. J Mol Biol. 1977 Apr. 15; 111 (3): 329-42

Non patent: Reference 5: Ho Y S, Duh J S, Jeng J H, Wang Y J, Liang Y C, Lin C H, Tseng C J, Yu C F, Chen R J, Lin J K. Griseofulvin potentiates antitumorigenesis effects of nocodazole through induction of apoptosis and G2/M cell cycle arrest in human colorectal cancer cells. Int J Cancer. 2001 Feb. 1; 91 (3): 393-401

Non patent Reference 6: Sorrentino L, Capasso F, Di Rosa M. Anti-inflammatory properties of griseofulvin. Agents Actions. 1977 March; 7 (I): 157-62

Non patent Reference 7: Sehgal V N, Bikhchandani R, Koranne R V, Nayar M, Saxena H M. Histopathological evaluation of griseofulvin therapy in lichen planus. A double-blind controlled study. Dermatologica. 1980; 161 (1): 22-7

Non patent Reference 8: Tamaki K, Osada A, Tsukamoto K, Ohtake N, Furue M. Treatment of plasma cell cheilitis with griseofulvin. J Am Acad Dermatol. 1994 May; 30 (5 Pt 1): 789-90

Non patent Reference 9: Tamaki K, Yasaka N, Osada A, Shibagaki N, Furue M. Successful treatment of pigmented purpuric dermatosis with griseofulvin. Br J Dermatol. 1995, January; 132 (1): 159-60

Non patent Reference 10: Cohen A, Goldman J, Daniels R, Kanenson W. Treatment of shoulder-hand syndrome with griseofulvdn. J Am Med Assoc. 1960 Jun. 4; 173: 542-3

Non patent Reference 11: Petersen A B, Ronnest M E, Larsen, T O, Clausen M E. The Chemistry of Griseofulvin. Chem. Rev. 2014 December; 114: 12088-12107

SUMMARY OF INVENTION

Technical Problem

The present invention provides a compound having a specific chemical structure having an anti-inflammatory activity which is useful as an active ingredient for preventing and treating an inflammatory disease, a pharmacologically acceptable salt thereof or the like, a novel production method therefor and an intermediate. Since the compound of the present invention or a pharmacologically acceptable salt thereof has different properties, in various aspects, from those of known anti-inflammatory drugs, the compound or a salt thereof is considered to be useful as a novel medicine.

Solution to Problem

The present inventors conducted intensive studies for developing a compound which is useful as an active ingredient for preventing and treating an inflammatory disease, a pharmacologically acceptable salt thereof or the like. As a result, they found the compound of the present invention, a pharmacologically acceptable salt thereof or the like. More specifically, the present invention is as described below.

[1]
A compound of general formula (1) or a pharmacologically acceptable salt thereof.

[Formula 1]

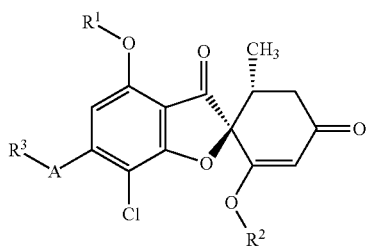

(1)

wherein the symbols in the formula are defined below:
R[1]: a C1-C6 alkyl group or a hydroxyC1-C6 alkyl group,
R[2]: a C1-C6 alkyl group,
A: a 5-membered aromatic heterocycle having bonds and having 1-4 atoms selected from the group consisting of a nitrogen atom, an oxygen atom and a sulfur atom; or an oxygen atom, and
R[3]: if A is a 5-membered aromatic heterocycle having bonds and having 1-4 atoms selected from the group consisting a nitrogen atom, as oxygen atom and a sulfur atom, then R[3] is a C1-C6 alkyl group, a hydroxyC1-C6 alkyl group or a C1-C6 alkoxyC1-C6 alkyl group; and if A is an oxygen atom, then R[3] is a hydroxyC1-C6 alkyl group or a C1-C6 alkoxyC1-C6 alkyl group.

[2]
A compound or a pharmacologically acceptable salt thereof according to [1], wherein R[1] is a methyl group, an ethyl group or a hydroxyethyl group.

[3]
A compound or a pharmacologically acceptable salt thereof according to [1] or [2], wherein R[2] is a methyl group.

[4]
A compound or a pharmacologically acceptable salt thereof according to any one of [1] to [3], wherein A a 5-membered aromatic heterocycle having bonds and having 1-4 atoms selected from the group consisting of a nitrogen atom, an oxygen atom and a sulfur atom; and R[3] is a methyl group, an ethyl group, a hydroxyC1-C3 alkyl group or a methoxyC1-C3 alkyl group.

[5]
A compound or a pharmacologically acceptable salt thereof according to any one of [1] to [4], wherein A a 5-membered aromatic heterocycle having bonds selected from the following group:

[Formula 2]

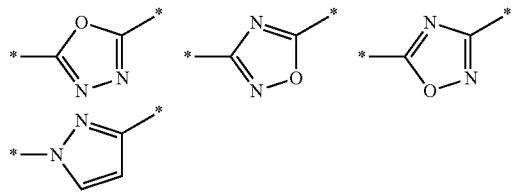

wherein * represents a bond.

[6]
A compound or a pharmacologically acceptable salt thereof according to any one of [1] to [3], in which A is an oxygen atom.

[7]
A compound of general formula or a pharmacologically acceptable salt thereof.

[Formula 3]

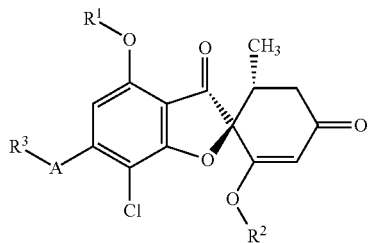

(1)

wherein the symbols in the formula are defined below:
R[1]: a methyl group, an ethyl group or a hydroxyethyl group,
R[2]: a methyl group,
A: a 5-membered aromatic heterocycle having bonds and selected from the following group:

[Formula 4]

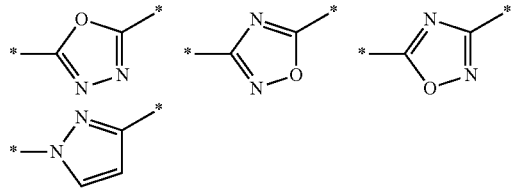

wherein * represents a bond,
R[3]: a methyl group, an ethyl group or a hydroxyC1-C3 alkyl group.

[8]
A compound or a pharmacologically acceptable salt thereof selected from the following group:
(2S,5'R)-7-chloro-6-(2-hydroxyethoxy)-3',4-dimethoxy-5'-methyl-spiro[benzofuran-2,4'-cyclohex-2-ene]-1',3-dione, (2S,5'R)-7-chloro-3',4-dimethoxy-6-(2-methoxyethoxy)-5'-methyl-spiro[benzofuran-2,4'-cyclohex-2-ene]-1',3-dione, (2S,5'R)-7-chloro-3',4-dimethoxy-5'-methyl-6-(1-methylpyrazol-3-yl)spiro[benzofuran-2,4'-cyclohex-2-ene]-1',3-dione, (2S,5'R)-7-chloro-6-(1-ethylpyrazol-3-yl)-3',4-dimethoxy-5'-methyl-spiro[benzofuran-2,4'-cyclohex-2-ene]-1',3-dione, (2S,5'R)-7-chloro-3',4-dimethoxy-5'-methyl-6-(5-methyl-1,3,4-oxadiazol-2-yl) spiro[benzofuran-2,4'-cyclohex-2-ene]-1',3-dione, (2S,5'R)-7-chloro-3',4-dimethoxy-5'-methyl-6-(3-methyl-1,2,4-oxadiazol-5-yl)spiro[benzofuran-2,4'-cyclohex-2-ene]-1',3-dione, (2S,5'R)-7-chloro-3',4-dimethoxy-5'-methyl-6-(5-methyl-1,2,4-oxadiazol-3-yl)spiro[benzofuran-2,4'-cyclohex-2-ene]-1',3-dione, (2S,5'R)-7-chloro-6-[5-(1-hydroxy-1-methyl-ethyl)-1,3,4-oxadiazol-2-yl]-3',4-dimethoxy-5'-methyl-spiro[benzofuran-2, 4'-cyclohex-2-ene]-1',3-dione, (2S,5'R)-7-chloro-6-[5-[(1S)-1-hydroxyethyl]-1,3,4-oxadiazol-2-yl]-3',4-dimethoxy-5'-methyl-spiro[benzofuran-2,4'-cyclohex-2-ene]-1',3-dione, (2S,5'R)-7-chloro-6-[5-[(1R)-1-hydroxyethyl]-1,3,4-oxadiazol-2-yl]-3',4-dimethoxy-5'-methyl-spiro[benzofuran-2,4'-cyclohex-2-ene]-1',3-dione, (2S,5'R)-7-chloro-4-ethoxy-6-[5-(1-hydroxy-1-methyl-ethyl)-1,3,4-oxadiazol-2-yl]-3'-methoxy-5'-methyl-spiro[benzofuran-2,4'-cyclohex-2-ene]-1',3-dione, (2S,5'R)-7-chloro-4-ethoxy-6-[5-[(1S)-1-hydroxyethyl]-1,3,4-oxadiazol-2-yl]-3'-methoxy-5'-methyl-spiro[benzofuran-2,4'-cyclohex-2-ene]-1',3-dione, (2S,5'R)-7-chloro-6-[3-(1-hydroxyethyl)-1,2,4-oxadiazol-5-yl]-3',4-dimethoxy-5'-methyl-spiro[benzofuran-2,4'-cyclohex-2-ene]-1',3-dione, (2S,5'R)-7-chloro-4-(2-hydroxyethoxy)-3'-methoxy-5'-methyl-6-(5-methyl-1,3,4-oxadiazol-2-yl)spiro[benzofuran-2,4'-cyclohex-2-ene]-1',3-dione, (2S,5'R)-7-chloro-4-(2-hydroxyethoxy)-3'-methoxy-5'-methyl-6-(3-methyl-1,2,4-oxadiazol-5-yl)spiro[benzofuran-2,4'-cyclohex-2-ene]-1',3-dione, and (2S,5'R)-7-chloro-4-(2-hydroxyethoxy)-3'-methoxy-5'-methyl-6-(5-methyl-1,2,4-oxadiazol-3-yl)spiro[benzofuran-2,4'-cyclohex-2-ene]-1',3-dione.

A pharmaceutical composition containing a compound or a pharmacologically acceptable salt thereof according to any one of [1] to [8] as an active ingredient.

[10]

A pharmaceutical composition according to [9], for preventing and/or treating an inflammatory disease.

[11]

A pharmaceutical composition according to [10], wherein the inflammatory disease is a disease selected from the group consisting of rheumatoid arthritis, systemic lupus erythematosus, scleroderma, bronchial asthma, asthmatic bronchitis, diffuse interstitial pneumonia, chronic obstructive pulmonary disease, ulcerative colitis, Crohn's disease, acute hepatitis, chronic hepatitis, fulminant hepatitis, autoimmune hepatitis, primary biliary cirrhosis, primary sclerosing cholangitis, alcoholic hepatitis, non-alcoholic steatohepatitis, cirrhosis, peripheral neuritis, ankylosing spondylitis, eczema (acute, subacute, chronic), contact dermatitis, sunlight (ultraviolet light) dermatitis, radiation dermatitis, atopic dermatitis, seborrheic dermatitis, psoriasis vulgaris, arthropathic psoriasis, psoriatic erythroderma, pustular psoriasis, lichen planus, erythema, rosacea, urticaria, alopecia areata, pemphigus, erythroderma, acne vulqaris, pressure sore, wound, burn, conjunctivitis, keratitis, scleritis, acute/chronic otitis media, perennial allergic rhinitis, hay fever, sinusitis, laryngitis, esophagitis, refractory stomatitis, glossitis, acute/chronic salivary gland inflammation, angular cheilitis, cheilitis, Behcet's disease, multiple sclerosis, Type I diabetes, Type II diabetes, atherosclerosis, pancreatitis and chronic heart failure.

[12]

A pharmaceutical composition according to [10], wherein the inflammatory disease is a disease selected from the group consisting of rheumatoid arthritis, systemic lupus erythematosus, bronchial asthma, acute hepatitis, autoimmune hepatitis, primary biliary cirrhosis, primary sclerosing cholangitis, alcoholic hepatitis, nonalcoholic steatohepatitis, ankylosing spondylitis, contact dermatitis, sunlight (UV) dermatitis, atopic dermatitis, seborrheic dermatitis, psoriasis vulgaris, arthropathic psoriasis, psoriatic erythroderma, pustular psoriasis, planus, erythema, rosacea, alopecia areata, pemphigus, erythroderma, acne vulgaris, pressure sore, wound, burn, sinusitis, laryngitis, esophagitis, refractory stomatitis, glossitis, acute/chronic salivary gland inflammation, angular cheilitis, cheilitis and Behcet's disease.

[13]

A pharmaceutical composition according to [10], wherein the inflammatory disease is a disease selected from the group consisting of rheumatoid arthritis, systemic lupus erythematosus, autoimmune hepatitis, alcoholic hepatitis, nonalcoholic steatohepatitis, ankylosing spondylitis, atopic dermatitis, psoriasis vulgaris, arthropathic psoriasis, psoriatic erythroderma, pustular psoriasis, lichen planus, pressure sore, wound, refractory stomatitis, glossitis and Behcet's disease.

[14]

A compound or a pharmacologically acceptable salt thereof according to any one of [1] to [8] for treating an inflammatory disease.

[15]

A method for administering an effective amount a pharmaceutical composition according to [9] for preventing and/or treating an inflammatory disease.

[16]

A TNF-α inhibitor containing a compound or a pharmacologically acceptable salt thereof according to any one of [1] to [8], as an active ingredient.

Advantageous Effects of the Invention

The compound of the present invention, a pharmacologically acceptable salt thereof or the like is useful as an active ingredient for preventing and/or treating an inflammatory disease. Examples of the inflammatory disease include rheumatoid arthritis, systemic lupus erythematosus, scleroderma, bronchial asthma, asthmatic bronchitis, diffuse interstitial pneumonia, chronic obstructive pulmonary disease, ulcerative colitis, Crohn's disease, acute hepatitis, chronic hepatitis, fulminant hepatitis, autoimmune hepatitis, primary biliary cirrhosis, primary sclerosing cholangitis, alcoholic hepatitis, non-alcoholic steatohepatitis, cirrhosis, peripheral neuritis, ankylosing spondylitis, eczema (acute, subacute, chronic), contact dermatitis, sunlight (ultraviolet light) dermatitis, radiation dermatitis, atopic dermatitis, seborrheic dermatitis, psoriasis vulgaris, arthropathic psoriasis, psoriatic erythroderma, pustular psoriasis, lichen planus, erythema, rosacea, urticaria, alopecia areata, pemphigus, erythroderma, acne vulgaris, pressure sore, wound, burn, conjunctivitis, keratitis, scleritis, acute/chronic otitis media, perennial allergic rhinitis, hay fever, sinusitis, laryngitis, esophagitis, refractory stomatitis, glossitis, acute/chronic salivary gland inflammation, angular cheilitis, cheilitis, Behcet's disease, multiple sclerosis, Type I diabetes, Type II diabetes, atherosclerosis, pancreatitis and chronic heart failure.

Preferred examples thereof include rheumatoid arthritis, systemic lupus erythematosus, bronchial asthma, acute hepatitis, autoimmune hepatitis, primary biliary cirrhosis, primary sclerosing cholangitis, alcoholic hepatitis, nonalcoholic steatohepatitis, ankylosing spondylitis, contact dermatitis, sunlight (UV) dermatitis, atopic dermatitis, seborrheic dermatitis, psoriasis vulgaris, arthropathic psoriasis, psoriatic erythroderma, pustular psoriasis, lichen planus, erythema, rosacea, alopecia areata pemphigus, erythroderma, acne vulgaris, pressure sore, wound, burn, sinusitis, laryngitis, esophagitis, refractory stomatitis, glossitis, acute/chronic salivary gland inflammation, angular cheilitis, cheilitis and Behcet's disease.

More preferred examples thereof include rheumatoid arthritis, systemic lupus erythematosus, autoimmune hepatitis, alcoholic hepatitis, nonalcoholic steatohepatitis, ankylosing spondylitis, atopic dermatitis, psoriasis vulgaris, arthropathic psoriasis, psoriatic erythroderma, pustular psoriasic, lichen planus, pressure sore, wound, refractory stomatitis, glossitis and Behcet's disease.

The present invention provides a novel and efficient method for producing the compound of the present invention or the like, and an intermediate. Accordingly, the present invention is advantageous in producing a medicinal drug.

DESCRIPTION OF EMBODIMENTS

Now, the present invention will be more specifically described below.
(Explanation of Substituents and Terms)
The present invention is directed to a compound of general formula (1) or a pharmacologically acceptable salt thereof.

[Formula 5]

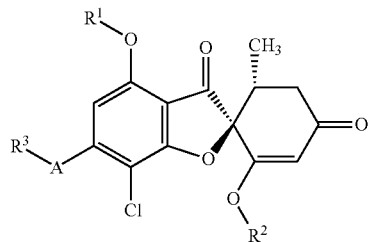

(1)

wherein the symbols in the formula are defined below:
$R^1$: a C1-C6 alkyl group or a hydroxyC1-C6 alkyl group,
$R^2$: a C1-C6 alkyl group,
A: a 5-membered aromatic heterocycle having bonds and having 1-4 atoms selected from the group consisting of a nitrogen atom, an oxygen atom and a sulfur atom, or an oxygen atom,
$R^3$: if A is a 5-membered aromatic heterocycle having bonds and having 1-4 atoms selected from the group consisting of a nitrogen atom, as oxygen atom and a sulfur atom, then $R^3$ is a C1-C6 alkyl group, a hydroxyC1-C6 alkyl group or a C1-C6 alkoxyC1-C6 alkyl group; and if A is an oxygen atom, then $R^3$ is a hydroxyC1-C6 alkyl group or a C1-C6 alkoxyC1-C6 alkyl group.

The C1-C6 alkyl group represented by $R^1$ is a linear or branched alkyl group having 1-6 carbon atoms and preferably a methyl group or an ethyl group.

The hydroxyC1-C6 alkyl group represented by $R^1$ is a linear or branched alkyl group having 1-6 carbon atoms substituted by a hydroxy group and preferably a hydroxyethyl group.

The C1-C6 alkyl group represented by $R^2$ is a linear or branched alkyl group having 1-6 carbon atoms and preferably a methyl group.

The C1-C6 alkyl group represented by $R^3$ is a linear or branched alkyl group having 1-6 carbon atoms and preferably a methyl or ethyl group.

The hydroxyC1-C6 alkyl group represented by $R^3$ is a linear or branched alkyl group having 1-6 carbon atoms substituted by a hydroxy group and preferably a hydroxyC1-C3 alkyl group. Examples thereof include a hydroxymethyl group, a 1-hydroxyethyl group, a hydroxyethyl group, a 1-hydroxy-1-methyl-ethyl group, a 1-hydroxypropyl group and 2-hydroxypropyl group.

The C1-C6 alkoxyC1-C6 alkyl group represented by $R^3$ is a linear or branched alkyl group having 1-6 carbon atoms substituted by a C7-C6 alkoxy group and preferably a methoxyC1-C3 alkyl group. Examples thereof include a methoxymethyl group, a 1-methoxyethyl group, a 2-methoxyethyl group, a 1-methoxypropyl group and a 2-methoxypropyl group.

The 5-membered aromatic heterocycle represented by A is a 5-membered aromatic heterocycle containing 1-4 atoms selected from the group consisting of a nitrogen atom, an oxygen atom and a sulfur atom, and having two bonds. Examples thereof include the following 5-membered aromatic heterocycles:

pyrrole, pyrazole, imidazole, 1,2,3-triazole, 1,2,4-triazole, tetrazole, furan, isoxazole, oxazole, 1,2,4-oxadiazole, 1,3,4-oxadiazole, 1,2,5-oxadiazole, thiophene, thiazole, isothiazole, 1,2,4-thiadiazole, 1,3,4-thiadiazole and 1,2,5-thiadiazole.

It is further preferred that the following 5 member rings are included.

[Formula 6]

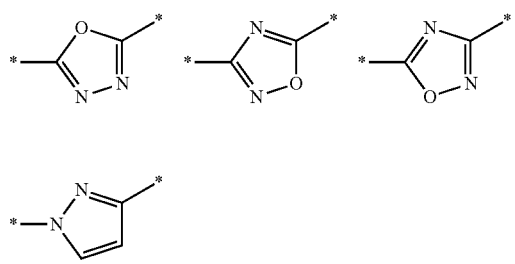

wherein * represents a bond.

The 5-membered aromatic heterocycles respectively form the following compounds serving as a compound of general formula (1), via the bonds.

[Formula 7]

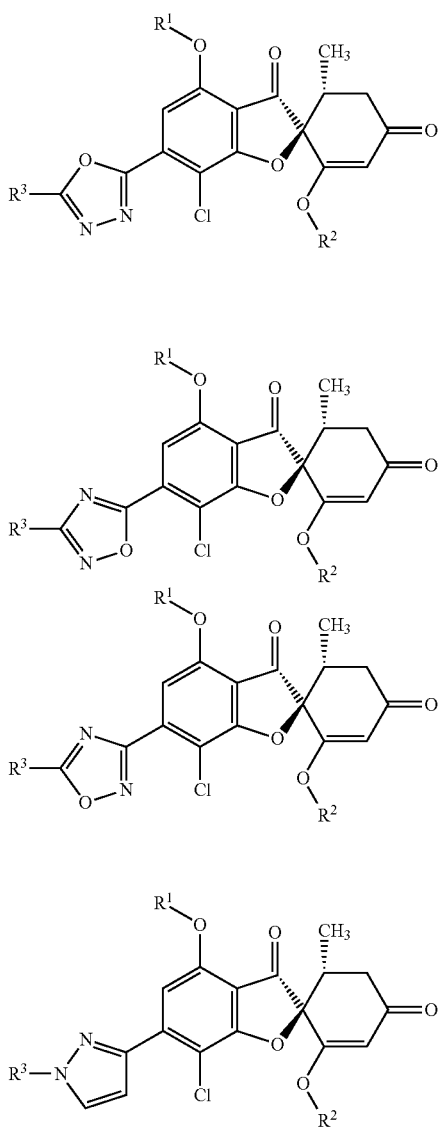

wherein R¹, R² and R³ are as defined above.

The term "pharmacologically acceptable salt thereof" refers to a salt which can be used as a medicinal drug. In the case of a compound having as acidic group or a basic group, a basic salt or an acid salt can be produced if a base or an acid is reacted with the group. The salt thus obtained represents a pharmacologically acceptable salt.

Examples of a pharmacologically acceptable "basic salt" of a compound preferably include an alkali metal salt such as a sodium salt, a potassium salt and a lithium salt; an alkaline earth metal salt such as a magnesium salt and a calcium salt; an organic base salt such as a N-methyl morpholine salt, a triethylamine salt, a tributylamine salt, a diisopropylethylamine salt, a dicyclohexylamine salt, a N-methyl piperidine salt, a pyridine salt, a 4-pyrrolidino-pyridine salt and a picoline salt; and an amino acid salt such as a glycine salt, a lysine salt, an arginine salt, an ornithine salt, glutamate and aspartate. Preferably, an alkali metal salt is mentioned.

Preferred examples of a pharmacologically acceptable "acid salt" of a compound include inorganic acid salts including a hydrohalic acid salt such as a hydrofluoride, a hydrochloride, a hydrobromide and a hydriodide, a nitrate, a perchlorate, a sulfate and a phosphate; organic acid salts including a lower alkanesulfonate such as a methanesulfonate, a trifluoromethanesulfonate and an ethanesulfonate, an aryl sultanate such as a benzenesulfonate and p-toluene sultanate, an acetate, a malate, a fumarate, a succinate, a citrate, an ascorbate, a tartrate, an oxalate and a maleate; and amino acid salts such as a glycine salt, a lysine salt, an arginine salt, an ornithine salt, a glutamate and an aspartate. Most preferably, a hydrohalic acid salt (particularly, hydrochloride) is mentioned.

The compound of the present invention or a pharmacologically acceptable salt thereof sometimes absorbs water or adsorbs moisture or forms a hydrate when it is left alone in the air or by re-crystallization. These various hydrates, solvates and polymorphic compounds are also included in the present invention.

The compound of the present invention, a pharmacologically acceptable salt thereof or a solvate thereof may have various type of isomers including geometric isomers such as a cis isomer and a trans isomer, tautomers, and optical isomers such as d-form and l-form depending on the types and combinations of substituents. However, unless otherwise specified, all isomers, stereoisomers and a mixture of these isomers and stereoisomers in any mixing ratio are included in the compound of the present invention. A mixture of these isomers can be separated by a separation means known in the art.

As the compound of the present invention, a labeled compound, more specifically, a compound having 1 or 2 or more atoms substituted with an isotope (for example, 2H, 3H, 13C, 14C, 35S), is also included.

In the present invention, a so-called prodrug is also included. The term prodrug refers to a compound having a group that can be converted into an amino group, a hydroxyl group or a carboxyl group by hydrolysis or in physiological conditions. The groups involved in forming such prodrugs are described in Prog. Med., vol. 5, 2157-2161 pages, 1985. More specifically, the prodrug can be as mentioned below.

If an amino group is present, e.g., a compound having an acylated, alkylated or phosphorylated amino group (for example, a compound having an eicosanoylated, alanylated, pentylaminocarbonylated, (5-methyl-2-oxo-1,3-dioxolen-4-yl) methoxycarbonylated, tetrahydrofuranylated, pyrrolidyl methylated, pivaloyloxymethylated or a tert-butylated amino group) can be mentioned.

If a hydroxyl group is present, e.g., a compound having an acylated, alkylated, phosphorylated or borated hydroxyl group (for example, a compound having an acetylated, palmitoylated, propanoylated, pivaloylated, succinylated, fumarylated, alanylated or dimethylaminomethylcarbonylated hydroxyl group) can be mentioned.

If a carboxy group is present, e.g., a compound having an esterified or amidated carboxy group (for example, a compound having an ethyl-esterified, phenyl-esterified, carboxymethyl-esterified, dimethylaminomethyl-esterified, pivaloyloxymethyl-esterified, ethoxycarbonyloxyethy-esterified, amidated or methlamidated carboxy group) can be mentioned.

(Production Method)

Now, the production method will be described. However, a method for producing a compound or a salt thereof is not limited by the methods described below.

[Method A]

Method A is a method of producing a compound (A-III) of the present invention

[Formula 8]

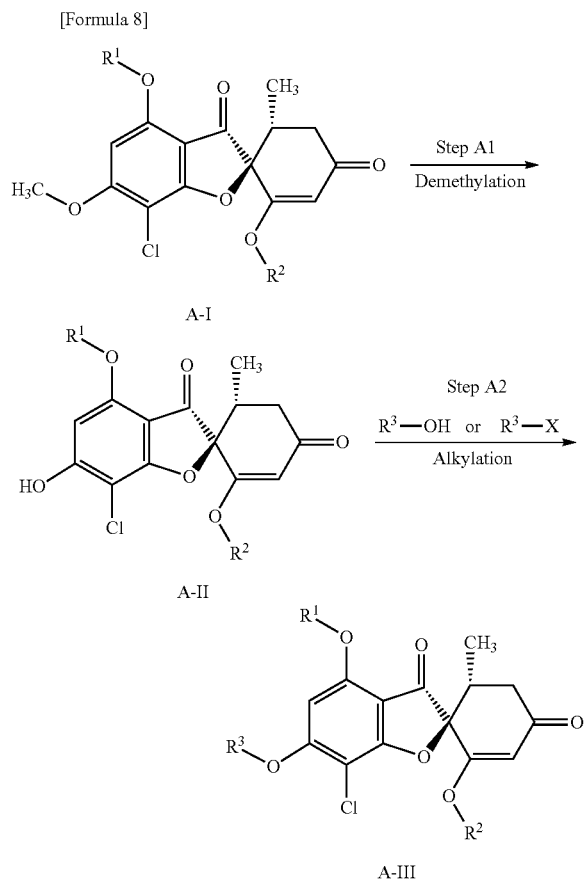

wherein $R^1$, $R^2$ and $R^3$ are the same as defined above; and X represents a leaving group such as a halogen group.

(Step A1) Demethylation Step

This is a step of obtaining a compound (A-II) from a compound (A-I) by use of a metal halide in the presence of a base and crown ether.

Examples of the base include triethylamine, diisopropylethylamine and pyridine.

Examples of the crown ether include 18-crown-6.

Examples of the metal halide include potassium iodide.

As a solvent, e.g., N,N-dimethylformamide may be mentioned or a solvent may not be used. The react temperature is usually about 60 to 120° C. and the reaction time is usually about 1 to 24 hours.

(Step A2) Alkylation Step (Case of Using Alkyl Halide)

This is a step of obtaining a compound (A-III) from a compound (A-II) by use of the corresponding alkylating reagent in the presence of a base.

Examples of the alkylating reagent include an alkyl halide such as an alkyl iodide and as alkyl bromide and a sulfonic acid ester such as an alkyl tosylate and an alkyl mesylate.

Examples of the base include triethylamine, diisopropylethylamine, and potassium carbonate.

As a solvent, tetrahydrofuran, 1,4-dioxane, acetonitrile, dichloromethane and N,N-dimethylformamide or a mixture of these can be mentioned. The reaction temperature is usually about 0 to 100° C. and the reaction time is usually about 0.5 to 24 hours.

(Case of using the Mitsunobu Reaction)

This is a step of obtaining a compound (A-III) from a compound (A-II) by use of the corresponding alcohol in the presence of a phosphine and an azodicarboxylate or a diazodicarboxamide.

Examples of the phosphine include triphenylphosphine and tri-n-butylphosphine.

Examples of the azodicarboxylate or diazodicarboxamide include diethyl azodicarboxylate, di-tert-butyl azodicarboxylate and 1,1'-(azodicarbonyl) dipyridine.

As a solvent, tetrahydrofuran, 1,4-dioxane, toluene or a mixture of these can be mentioned. The reaction temperature is usually about 0 to 100° C. and the reaction time is usually about 0.5 to 24 hours.

[Method B]

Method B is a method of producing a compound (B-III) (equivalent to the compound (A-I) that is used in Method A). If $R^1$ is a methyl group, a compound. (B-III) can be produced without employing these steps.

[Formula 9]

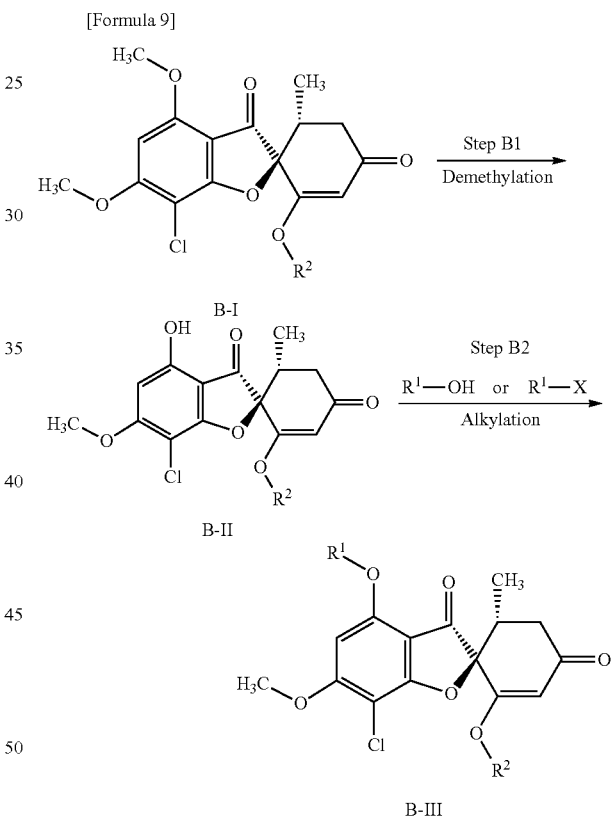

wherein $R^1$, $R^2$ and X are the same as defined above.

(Step B1) Demethylation Step

This is a step of obtaining a compound (B-II) from a compound (B-I) by use of a metal halide.

Examples of the metal halide include magnesium iodide.

As a solvent, toluene, tetrahydrofuran, 1,4-dioxane or a mixture of these can be mentioned.

The reaction temperature is usually about 60 to 120° C. and the reaction time is usually about 0.5 to 24 hours.

(Step B2) Phenol Alkylation Step

This is a step of obtaining a compound (B-III) from a compound (B-II) in the same manner as in (Step A2).

[Method C]

Method C is a method of producing a compound (C-III) of the present invention from compound (C-I) (equivalent to compound (A-II) that is used in Method A).

[Formula 10]

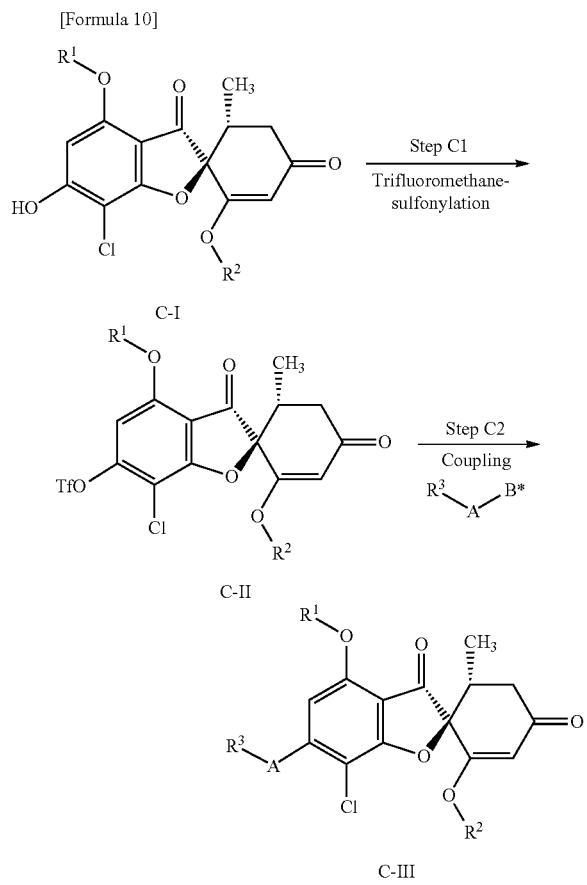

wherein $R^1$, $R^2$, $R^3$ and A are the same as defined above; Tf represents a trifluoromethanesulfonyl group; and $B^+$ represents a borono group (—B(OH)$_2$) or a 4,4,5,5-tetramethyl-1,3,2-dioxaboran-2-yl group.

(Step C1) Trifluoromethanesulfonylation Step

This is a step of obtaining a compound (C-II) from a compound (C-I) by use of a trifluoromethanesulfonylating reagent in the presence of a base.

Examples of the trifluoromethanesulfonylation reagent include trifluoromethanesulfonic anhydride, trifluoromethanesulfonic chloride and N-phenylbis(trifluoromethanesulfonimide).

Examples of the base include triethylamine and diisopropylethylamine.

As a solvent, tetrahydrofuran, 1,4-dioxane, acetonitrile, dichloromethane or a mixture of these can be mentioned.

The reaction temperature is usually, −20° C. to about room temperature and the reaction time is usually about 0.5 to 24 hours.

(Step C2) Step of Coupling Reaction using Transition Metal Catalyst

This is a step of obtaining a compound (C-III) from a compound (C-II) by use of a palladium catalyst and $R^3$-A-$B^+$ in the presence of a base.

Examples of the palladium catalyst include tetrakis (triphenylphosphine)palladium, [1,1'-bis(diphenylphosphino) ferrocene] dichloropalladium, tris(dibenzylideneacetone)dipalladium, palladium acetate, acetylacetone palladium and bis(triphenylphosphine)palladium dichloride.

Examples of the base include triethylamine, diisopropylethylamine, 1,8-diazabicyclo[5.4.0]-7-undecene (DBU), 1,5-diazabicyclo[4.3.0]-5-nonen (DEN), potassium hydrogen carbonate, sodium hydrogen carbonate, potassium carbonate, sodium carbonate, potassium hydroxide, sodium hydroxide, potassium phosphate and sodium phosphate.

As a solvent, methanol, ethanol, tetrahydrofuran, 1,4-dioxane, water, N,N-dimethylformamide, dimethylsulfoxide, toluene or a mixture of these can be mentioned.

The reaction temperature is usually about 60 to 120° C. and the reaction time is usually about 0.5 to 12 hours.

[Method D]

Method D is a method of producing a compound (D-IV) of the present invention from a compound. (D-I) (equivalent to the compound (C-II) that is used in Method C).

[Formula 11]

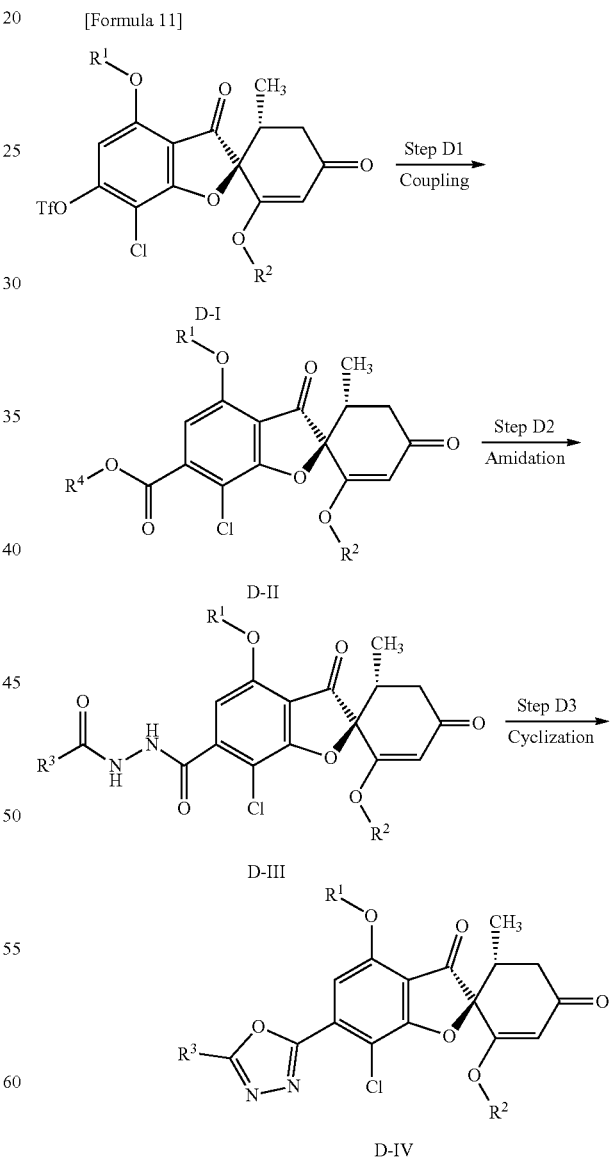

wherein $R^1$, $R^2$, $R^3$ and Tf are the same as defined above and $R^4$ represents a phenyl group that may have a substituent.

(Step D1) Step of Coupling with Formate

This is a step of obtaining a compound (D-II) from a compound. (D-I) by use of a formate in the presence of a base and a palladium catalyst (phosphine ligand).

Examples of the base include triethylamine, diisopropylethylamine, dimethylaminopyridine, potassium carbonate, sodium carbonate, potassium hydroxide and sodium hydroxide.

Examples of the formate include phenyl formate and (2,4,6-trichlorophenyl) formate.

Examples of the palladium catalyst include palladium acetate, acetylacetone palladium, palladium trifluoroacetate, palladium dichloride, tris(dibenzylideneacetone)dipalladium or bis(triphenviphosphine)palladium dichloride.

Examples of the phosphine ligand to be used simultaneously with the palladium catalyst include 4,5-bis(diphenylphosphino)-9,9-dimethylxanthene (xantphos), 1,1'-bis(diphenylphosphino)ferrocene (dppf), 2,2'-bis(diphenylphosphino)-1,1-binaphthyl (BINAP), bis(diphenylphosphino)methane (DPPM), triphenylphosphine and 1,2-bis(diphenylphosphino)ethane (DPPE).

As a solvent, N,N-dimethylformamide, toluene, tetrahydrofuran, acetonitrile or a mixture of these can be mentioned.

The reaction temperature is usually about room temperature to 120° C. and the reaction time is usually about 1 to 8 hours.

(D2 Step) Step of Amidation with Acyl Hydrazine

This is a step of obtaining a compound (D-III) from a compound (D-II) by use of the corresponding acyl hydrazine in the presence of a base.

Examples of the base include triethylamine, diisopropylethylamine, dimethylaminopyridine, potassium carbonate, sodium carbonate, potassium hydroxide and sodium hydroxide. An additive such as N-hydroxysuccimmide (HOSu), 1-hydroxybenzotriazole (HOBt) and 1-hydroxy-7-azabenzotriazole (HOAt) is sometimes advantageously used in order to make the reaction progress smoothly.

As a solvent, N,N-dimethylformamide, dichloromethane, tetrahydrofuran, acetonitrile or a mixture of these can be mentioned.

The reaction temperature is usually about 0 to 60° C. and the reaction time is usually about 1 to 12 hours.

(Step D3) Cyclization Step

This is a step of obtaining a compound (D-IV) from a compound (D-III) by use of a dehydrating agent.

Examples of the dehydrating agent include (methoxycarbonylsulfamoyl) triethylammonium hydroxide inner salt, phosphoryl chloride, polyphosphoric acid, sulfuric acid, triphenylphosphine/iodine, tosylate and tosyl chloride.

As a solvent, toluene, acetonitrile, dichloromethane or a mixture of these solvents can be mentioned. A solvent may not be used.

The reaction temperature is usually about 0 to 100° C. and the reaction time is usually about 0.5 to 24 hours.

[Method E]

Method E is a method of producing a compound (E-III) of the present invention from a compound (E-I) (equivalent to the compound (D-II) that is used in Method D).

[Formula 12]

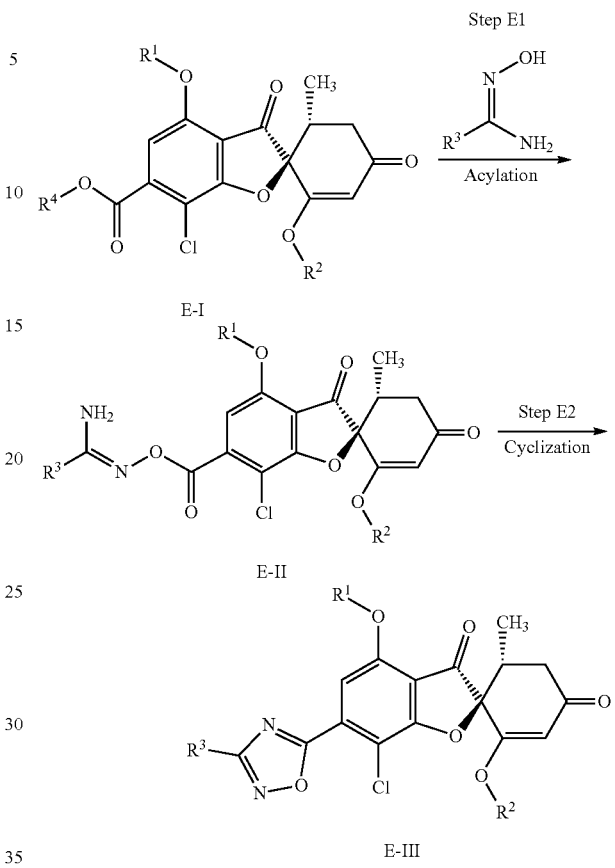

wherein $R^1$, $R^2$, $R^3$ and $R^4$ are the same as defined above.

(Step E1) Step of Acylation with Amidoxime

This is a step of obtaining a compound (E-II) from a compound (E-I) by use of the corresponding amidoxime in the presence of a base.

Examples of the base include triethylamine, diisopropylethylamine, dimethylaminopyridine, potassium carbonate, sodium carbonate, potassium hydcroxide and sodium hydroxide. An additive such as N-hydroxysuccinimide (HOSu), 1-hydroxybenzotriazole (HOBt) and 1-hydroxy-7-azabenzotriazole (HOAt) is sometimes advantageously used iii order to make the reaction progress smoothly.

As a solvent, N,N-dimethylformamide, dichloromethane, tetrahydrofuran, acetonitrile or a mixture of these can be mentioned.

The reaction temperature is usually about room temperature to 80° C. and the reaction time is usually about 1 to 12 hours.

(Step E2) Cyclizaton Step

This is a step of obtaining a compound (E-III) by stirring a compound (E-II) in a solvent at room temperature or under heating.

As the solvent, toluene, N,N-dimethylformamid, dichloromethane, tetrahydrofuran, acetonitrile or a mixture of these can be mentioned.

The reaction temperature is usually about room temperature to 100° C. and the reaction time is usually about. 0.5 to 24 hours.

[Method F]

Method F is a method of producing a compound (F-V) of the present invention from a compound. (F-I) (equivalent to the compound (C-II) that is used in Method C).

[Formula 13]

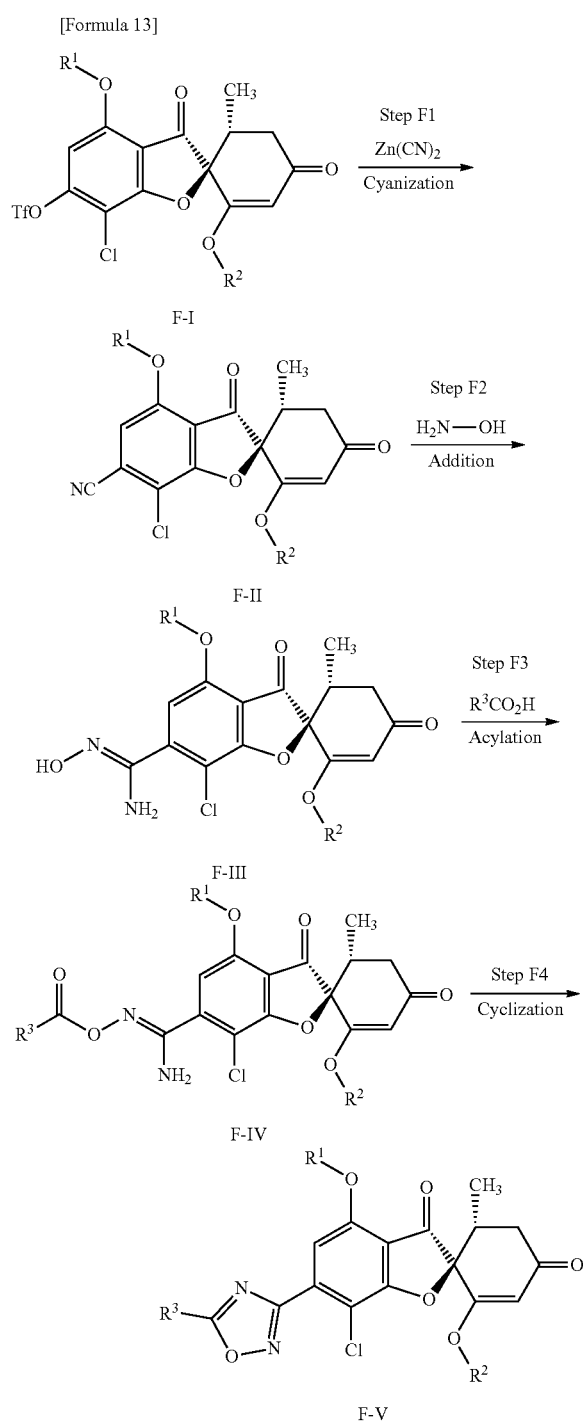

wherein R¹, R²R³, and Tf are the same as defined above.

(Step F1) Step of Cyanization using a Transition Metal Catalyst

This is a step of obtaining a compound (F-II) from a compound (F-I) in the presence of zinc cyanide and a palladium catalyst and in the presence or absence of a phosphine.

Examples of the palladium catalyst include tris(dibenzylideneacetone) dipalladium, bis[tri(tert-butyl]phosphine) palladium, tetrakis (triphenylphosphine)palladium and bis (trifluoroacetoxy)palladium.

Examples of the phosphine include triphenylphosphine, tri(tert-butyl)phosphine, tri-o-toluylphosphine, diphenylphosphinoferrocene and diphenylphosphinobutane. As a solvent, N-methyl-2-pyrrolidone or N,N-dimethyl formamide or a mixture of these can be mentioned.

The reaction temperature is usually about 80 to 120° C. and reaction time is usually about 1 to 8 hours.

(Step F2) Step of Adding Hydroxylamine

This is a step of obtaining a compound (F-III) from a compound (F-II) by use of a hydroxylamine.

As a solvent, methanol, ethanol, dimethylsulfoxide, water or a mixture of these solvents can be mentioned.

The reaction temperature is usually about room temperature to 100° C. and the reaction time is usually about 0.5 to 24 hours.

(Step F3) Step of Acylating Oxime

This is a step of obtaining a compound (F-IV) from a compound (F-III) by use of the corresponding carboxylic acid in the presence of a condensing agent and a base.

Examples of the condensing agent include 0-(7-azabenzotriazol-1-yl)-N,N,N',N'-tetramethylhonium hexafluorophosphate (HATU), 4-(4,6-dimethoxy-1,3,5-triazin-2-yl)-4-methylmorpholine (DMT-MM) and 1-(3-dimethylaminopropyl)-3-ethylcarbodiimide (WSC or EDCI).

Examples of the base include triethylamine, diisopropylethylamine and dimethylaminopyridine.

An additive such as N-hydroxysuccinimide (HOSu), 1-hydroxybenzotriazole (HOBt) and 1-hydroxy-7-azabenzotriazole (HOAt) is sometimes advantageously used in order to make the reaction progress smoothly.

As a solvent, ethanol, tetrahydrofuran, acetonitrile, N,N-dimethylformamide, dichloromethane, toluene or a mixture of these solvents can be mentioned.

The reaction temperature is usually about room temperature to 60° C. and the reaction time is usually about 0.5 to 24 hours.

(Step F4) Cyclization Step

This is a step of obtaining a compound (F-V) by stirring a compound (F-IV) in a solvent at room temperature or under heating.

As the solvent, toluene, N,N-dimethylformamide, dichloromethane, tetrahydrofuran, acetonitrile or a mixture of these can be mentioned.

The reaction temperature is usually about 60 to 120° C. and the reaction time is usually about 0.5 to 24 hours.

[Method G]

Method G is a method of producing a compound (G-III) of the present invention from a compound (G-1).

[Formula 14]

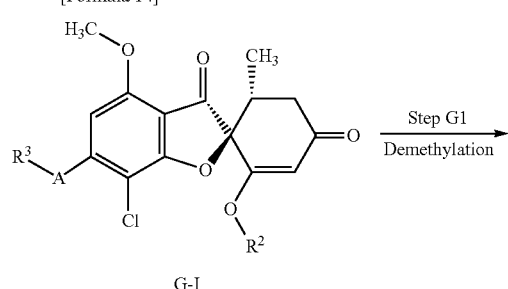

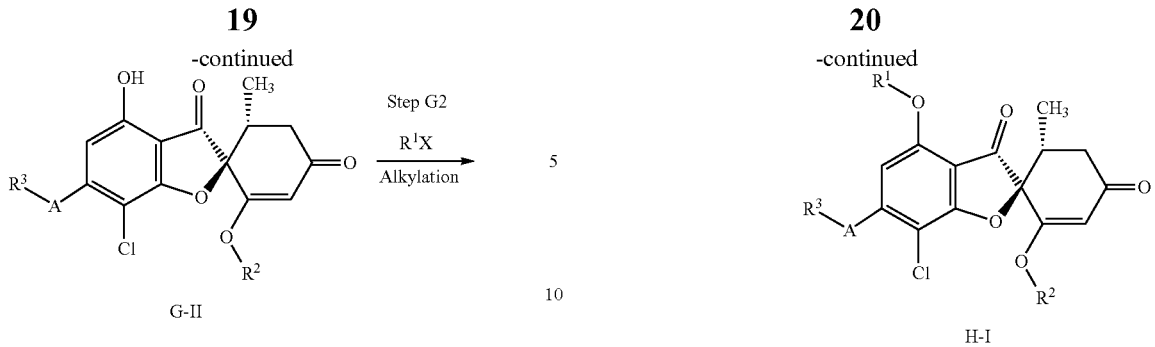

G-II

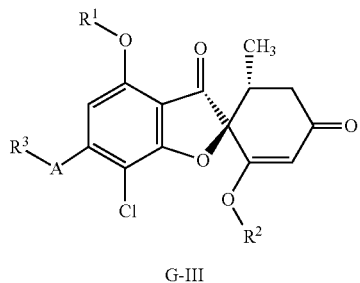

G-III wherein $R^1$, $R^2$, $R^3$, A and X are the same as defined above.

(Step G1) Demethylation Step

This is a step of obtaining a compound (G-II) from a compound. (G-I) in the same manner as in (Step B1).

(Step G2) Alkylation Step

This is a step of obtaining a compound (G-III) from a compound (G-II) in the same manner as in (Step A2).

[Method H]

Method H is a method of producing a compound (H-I) of the present invention from a compound (H-II) by removing a protecting group contained in $R^{1'}$ or $R^{3'}$ to convert it into $R^1$ or $R^3$.

[Formula 15]

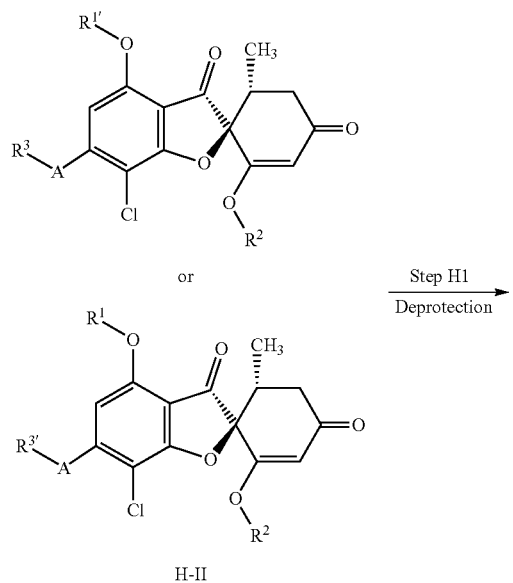

H-II wherein $R^1$, $R^2$, $R^3$ and A are the same as defined above; $R^{1'}$ and $R^{3'}$ represent protected $R^1$ and $R^3$, for example, a hydroxyC1-C6 alkyl group protected with a protecting group such as a tetrahydropyranyl group and a t-butyldimethylsilyl group, if $R^1$ is a hydroxyC1-C6 alkyl group.

(H1 Step) Deprotection Step (Case of Tetrahydropyranyl (THP) Group)

This is a step of obtaining a compound (H-II) from a compound (H-I) containing a hydroxy group protected with a tetrahydropyranyl group by use of an acid.

Examples of the acid include hydrochloric acid, sulfuric acid, hydrochloric acid-methanol, hydrochloric acid-1,4-dioxane, hydrochloric acid-ethyl acetate, acetic acid, p-toluenesulphonic acid and pyridinium p-toluenesulfonate.

As a solvent, methanol, ethanol, tetrahydrofuran, water or a mixture of these can be mentioned.

The reaction temperature is usually about 0 to 80° C. and the reaction time is usually about 0.5 to 24 hours.

(Case of Silyl Group)

In this step, the silyl group refers to a silyl group that is generally used as a protecting group in synthesis, such as a trimethylsilyl group and a t-butyldimethylsilyl group.

This is a step of obtaining a compound (H-II) from a compound (H-I) containing a hydroxy group and protected with a silyl group by use of a desilylation reagent.

Examples of the desilylation reagent include an acid and tetrabutylammonium fluoride (TRAF), hydrogen fluoride and hydrogen fluoride pyridine.

Examples of the acid include hydrochloric acid, sulfuric acid, hydrochloric acid-methanol, hydrochloric acid-1,4-dioxane, hydrochloric acid-ethyl acetate, acetic acid, p-toluenesulfonic acid and trifluoro acetic acid. The acid can be used in a reaction in a catalytic amount.

As a solvent, methanol, ethanol, tetrahydrofuran, 1,2-dimethoxyethane, 1,4-dioxane, acetonitrile, water or a mixture of these can be mentioned.

The reaction temperature is usually about 0 to 60° C. and the reaction time is usually about 0.5 to 24 hours.

The compounds produced by the above methods can be isolated and purified by a method known in the art, such as extraction, precipitation, distillation, chromatography, fractional recrystallization and recrystallization.

If a compound or an intermediate has an asymmetric carbon, it has optical isomers. These optical isomers can be mutually isolated and purified by a conventional method such as fractional recrystallization (salt fractionation) using recrystallization with a proper salt, and column chromatography. For a method of fractionating an optical isomer from a racemic body, refer to the document: J. Jacques et al, "Enantiomers, Racemates and Resolution, John Wiley And Sons, Inc.".

(Dosage Form)

As an administration route, oral administration using a tablet, a pill, a capsule, a granule, a powder or a liquid; or parenteral administration using an injection such as intra-articular, intravenous or intramuscular injections, a suppository, an eye drop, an eye ointment, a transdermal liquid, an ointment, a transdermal patch, a transmucosal liquid, a transmucosal patch or an inhalant, may be employed.

As a solid composition for oral administration, e.g., tablets, powders and granules are used. In such a solid composition, one or two or more active ingredients are mixed with at least one type of inactive excipient such as lactose, mannitol, dextrose, hydroxypropyl cellulose, microcrystalline cellulose, starch, polyvinylpyrrolidone and/or magnesium aluminometasilicate. In such a composition, an inactive additive such as a lubricant (e.g., magnesium stearate), a disintegrant such as sodium carboxymethyl starch, a stabilizer and/or a solubilizer, may be added in accordance with a conventional method. Tablets or pills, if necessary, may be coated with sugar, a film soluble in the stomach or an enteric film.

Examples of a liquid composition for oral administration include a pharmacologically acceptable emulsion, solution, suspension, syrup and elixir. Such a liquid composition contains an inactive diluent that is generally used, such as purified water or ethanol. The liquid composition may contain an additive such as a solubilizer, a wetting agent or a suspending agent, a sweetener, a flavor, an aroma material or an antiseptic agent, other than the inactive diluent.

Examples of an injection for parenteral administration include an aqueous or non-aqueous aseptic solution, suspension and emulsion. Examples of the aqueous solvent include distilled water for injection and physiological saline. Examples of the nonaqueous solvent include propylene glycol, polyethylene glycol, a vegetable oil such as olive oil, an alcohol such as ethanol and Polysorbate 80. Such a composition may further contain a tonicity agent, a preservative, a wetting agent, an emulsifying agent, a dispersant, a stabilizer or a solubilizing agent. Such a composition is sterilized, for example, by filtration through a sterilization filter, addition of a disinfectant or irradiation. Alternatively, an aseptic solid composition is produced and dissolved or suspended in aseptic water or aseptic solvent for injection just before use and then put in use.

Examples of an external formulation include an ointment, a plaster, a cream, a jelly, a cataplasm, a spray, a lotion, an eye drop and an eye ointment. Such an external formulation contains, e.g., an ointment base, a lotion base, an aqueous or non-aqueous solution, a suspension or an emulsion that is generally used. Examples of the ointment or lotion base include polyethylene glycol, propylene glycol, white petrolatum, beeswax, polyoxyethylene hydrogenated castor oil, glyceryl monostearate, stearyl alcohol, cetyl alcohol, lauromacrogol and sorbitan sesquioleate.

As an inhalation and a transmucosal agent such as a Transvaal agent, a solid, liquid or semi-solid composition is used and can be produced by a method known in the art. Such an agent may appropriately contain, for example, an excipient known in the art, further, a pH adjuster, a preservative, a surfactant, a lubricant, a stabilizer or a thickener. An appropriate device for inhalation or insufflation can be used for administration; more specifically, a device known in the art such as a metered dose inhalation device or a spray is used. A compound (of the invention) may be administered alone or as a composition, in the form of powder; or used in combination with a pharmaceutically acceptable carrier in the form of a solution or suspension. An inhaler such as a dry powder inhaler may be used for single administration or multiple administrations. A dry powder or a powder-containing capsule can be used. Alternatively, the inhaler may be a pressurized aerosol spray using an appropriate propellant, i.e., a suitable gas such as chlorofluoroalkane, hydrofluoroalkane or carbon dioxide.

(Dosage Amount)

In the case of oral administration, the proper dosage amount per day per weight is generally about 0.001-100 mg/kg, preferably 0.1-30 mg/kg, and more preferably 0.1-10 mg/kg. This is administered in a single dose or in two or more doses. In the case of intravenous administration, the proper dosage amount per day per weight is about 0.0001-10 mg/kg and administered in a single dose per day or in a plurality of doses. In the case of a transmucosal agent, the dosage amount per weight is about 0.001-100 mg/kg, which is administered in a single dose or in a plurality of doses. The dosage amount is appropriately and individually determined in consideration of the symptoms, age and sex of the (Combined Use)

In the present invention, the compound of the invention can be used in combination with various types of therapeutic agents or prophylactic agents expected to have an effect on a disease. The agent to be used in combination may be administered simultaneously or sequentially or intermittently at desired time intervals. The formulations to be simultaneously administered may be a combination drug or separate drugs.

Formulation Example 1

Powdered Medicine

The compound of the present invention (5 g), lactose (895 g) and corn starch (100 g) were mixed in a blender to obtain powdered medicine.

Formulation Example 2

Granule

The compound of the present invention (5 g), lactose (865 g) and low substituted hydroxypropyl cellulose (100 g) were mixed and then a 10% aqueous solution of hydroxypropyl cellulose (300 g) was added thereto and the mixture was kneaded, granulated by an extrusion granulator, and dried to obtain granules.

Formulation Example 3

Tablet

The compound of the present invention (5 g), lactose (90 g), corn starch (34 g), crystalline cellulose (20 g) and magnesium stearate (1 g) were mixed in a blender and compressed into tablets by a tablet machine to obtain tablets.

Pharmacological activity of the compound of the present invention or a pharmacologically acceptable salt thereof was checked by the following test.

(Test Example) Determination of TNF-α Inhibition Rate

A test substance was suspended in a 0.5% (w/v) methyl cellulose and orally administered to mice at a dose of 100 mg/kg. One hour later, a lipopolysaccharide (LPS, Sigma-Aldrich, L2630 (trade name)) (0.4 mg/kg) was intraperitoneally administered to induce inflammation. One hour after administration of LPS, blood was taken from the vena cava under anesthesia with isoflurane, placed in a tube containing a serum separating agent, allowed to stand still at room temperature for 20-30 minutes and centrifuged at 4° C. at 12,000 rpm for 5 minutes to obtain the serum. Thereafter, the amount of the TNF-α in the serum was measured by using Mouse INF-α Elisa. Kit (Invitrogen, KMC3011C (trade name)) or Mouse TNF-α Immunoassay Kit (PerkinElmer, AL505 (trade name)) in accordance with the protocol of the kit. The serum was diluted 10 times with the dilution solution contained in the kit and put in use.

TNF-α inhibition rate (%) of the test substance was calculated in accordance with the following expression.

TNF-α inhibition rate (I)=[(TNF-α amount of control group)−(TNF-α amount of test substance administration group)]×100/(TNE-α amount of control group)

TABLE 1

| Example No. | TNF-α inhibition rate (%) |
|---|---|
| Griseofulvin | 19 |
| 1 | 62 |
| 2 | 71 |
| 3 | 65 |
| 4 | 73 |
| 5 | 70 |
| 6 | 55 |
| 7 | 65 |
| 8 | 38 |
| 9 | 65 |
| 10 | 58 |
| 11 | 61 |
| 12 | 61 |
| 13 | 82 |
| 14 | 24 |
| 15 | 55 |
| 16 | 62 |

EXAMPLES

Now, the present invention will be more specifically described by way of Examples and the Test Example. However, the present invention is not limited by these.

In the following Examples, nuclear magnetic resonance (hereinafter referred to as $^1$H NMR) spectra were obtained by using tetramethylsilane as a standard substance and chemical shift values were expressed by δ values (ppm). In a splitting pattern, a singlet was represented by s, a doublet d, a triplet t, a quartet q, a multiplet m and a broad br.

Example 1

(2S,5'R)-7-Chloro-6-(2-hydroxyethoxy)-3',4-dimethoxy-5'-methyl-spiro[benzofuran-2,4'-cyclohex-2-ene]-1',3-dione 1a (2S,5'R)-7-Chloro-6-hydroxy-3',4-dimethoxy-5'-methyl-spiro[benzofuran-2,4'-cyclohex-2-ene]-1',3-dione (+)-Griseofulvin (CAS number: 126-07-8, product code: G0384 (manufactured by Tokyo Kasei Kogyo Co., Ltd.)) (50 g), potassium iodide (23.5 g) and 18-crown-6-ether (41.2 g) were dissolved in pyridine (500 mL), stirred at 120° C. for 9 hours and allowed to stand still at room temperature overnight.

The reaction mixture was concentrated. To this, aqueous 4% sodium bicarbonate was added. The reaction mixture was washed twice with ethyl acetate. The aqueous layer was neutralized with 1 mol/l hydrochloric acid and extracted with ethyl acetate. The organic layer was washed with water and saturated saline and dried over anhydrous sodium sulfate. The solvent was distilled away under reduced pressure and the resultant residue was purified by silica gel column chromatography [elution solvent: dichloromethane/ethanol=99/1 (V/V)] to obtain a crude product (19.4 g)

Ethyl acetate was added to the crude product to solidify it. The mixture was subjected to filtration to obtain the title compound (15.2 g (yield: 32%)) as a white solid.

1b (2S,5'R)-7-Chloro-6-(2-hydroxyethoxy)-3',4-dimethoxy-5'-methyl-spiro[benzofuran-2,4'-cyclohex-2-ene]-1',3-3-dione The compound of Example 1 (1a): (2S,5'R)-7-chloro-6-hydroxy-3',4-dimethoxy-5'-methyl-spiro[benzofuran-2,4'-cyclohex-2-ene]-1',3-dione (0.1 g) was dissolved in N,N-dimethylformamide (3 mL). To this, 2-bromoethanol (0.0738)) and potassium carbonate (0.102 g) were added and stirred at 100° C. for 6 hours.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: ethyl acetate] to obtain the title compound (38 mg (yield: 34%)) as a light yellow solid.

Example 2

(2S,5'R)-7-Chloro-3',4-dimethoxy-6-(2-methoxyethoxy)-5'-methyl-spiro[benzofuran-2,4'-cyclohex-2-ene]-1',3-dione The compound of Example 1 (1a): (2S,5'R)-7-chloro-6-hydroxy-3',4-dimethoxy-5'-methyl-spiro[benzofuran-2,4'-cyclohex-2-ene]-1',3-dione (30 mg) was dissolved in N,N-dimethylformamide (1 mL). To this, 2-bromoethyl methyl ether (136 rag) and potassium carbonate (135 mg) were added. The reaction mixture was stirred at 80° C. for 6 hours.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: ethyl acetate] to obtain the title compound (20 mg (yield: 57%)) as a white solid.

Example 3

(2S,5'R)-7-Chloro-3',4-dimethoxy-5'-methyl-6-(1-methylpyrazol-3-yl)spiro[benzofuran-2,4'-cyclohex-2-ene]-1',3-dione 3a

[(2S,5'R)-7-Chloro-1',4-dimethoxy-5'-methyl-3,3'-dioxo-spiro[benzofuran-2,6'-cyclohexene]-6-yl]trifluoromethanesulfonate The compound of Example 1 (1a): (2S,5'R)-7-chloro-6-hydroxy-3',4-dimethoxy-5'-methyl-spiro[benzofuran-2,4'-cyclohex-2-ene]-1',3-dione (20 g) was dissolved in dichloromethane (300 mL). To this, N-phenylbis(trifluoromethanesulfonimide) (25.3 g) and triethylamine (20.6 mL) were added. The reaction solution was allowed to stand still at room temperature overnight.

The reaction solution was diluted with dichloromethane. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=8/2–3/7 (V/V)] to obtain the title compound (23.5 g (yield: 852)) as a white solid.

3b (2S,5'R)-7-Chloro-3',4-dimethoxy-5'-methyl-6-(1-methylpyrazol-3-yl)spiro[benzofuran-2,4'-cyclohex-2-ene]-1',3-dione The compound of Example 3 (3a): [(2S,5'R)-7-chloro-1',4-dimethoxy-5'-methyl-3,3'-dioxo-spiro[benzofuran-2,6'-cyclohexene]-6-yl] trifluoromethanesulfonate (76 mg) was dissolved in N,N-dimethylformamide (1.6 mL). To this, 1-methyl-3-(4,4,5,5-tetramethyl-1,3,2-dioxaborolan-2-yl)-1H-pyrazole (0.0403)), potassium carbonate (0.0669 g) and [1,1'-bis(diphenylphosphino)ferrocene]palladium (II) dichloride dichloromethane additive (0.0131 g) were added at room temperature. The mixture was stirred at 80° C. for 3 hours.

After the temperature of the reaction mixture had returned to room temperature, the reaction mixture was diluted with ethyl acetate and insoluble matter was filtered off. The filtrate was poured into water and extracted with ethyl acetate. The organic layer was washed with water and saturated saline and (tried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (27 mg (yield: 42%)) as a white solid.

Example 4

(2S,5'R)-7-Chloro-6-(1-ethylpyrazol-3-yl)-3',4-dimethoxy-5'-methyl-spiro[benzofuran-2,4'-cyclohex-2-ene]-1',3-dione The compound of Example 3 (3a): [(2S,5'R)-7-chloro-1',4-dimethoxy-5'-methyl-3,3'-dioxo-spiro[benzofuran-2,6'-cyclohexene]-6-yl] trifluoromethanesulfonate (0.5 g) was dissolved in toluene (10 mL). To this, 1-ethyl-3-(4,4,5,5-tetramethyl-1,3,2-dioxaborolan-2-yl)-1H-pyrazole (0.283 g), chloro(2-dicyclohexylphosphino-2',4',6'-triisopropyl-1,1'-biphenyl)[2-(2'-amino-1,1'-biphenyl)]palladium (II) (0.167 g) and saturated aqueous solution of sodium hydrogen carbonate (5 mL) were added. The reaction mixture was stirred at 90° C. for two hours.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (266 mg (yield: 60%)) as a white solid.

Example 5

(2S,5'R)-7-Chloro-3',4-dimethoxy-5'-methyl-6-(5-methyl-1,3,4-oxadiazol-2-yl)spiro[benzofuran-2,4'-cyclohex-2-ene]-1',3-dione 5a (2,4,6-Trichlorophenyl) (2S,5'R)-7-chloro-1',4-dimethoxy-5'-methyl-3,3'-dioxo-spiro[benzofuran-2,6'-cyclohexene]-6-carboxylate The compound of Example 3 (3a): [(2S,5'R)-7-chloro-1',4-dimethoxy-5'-methyl-3,3'-dioxo-spiro[benzofuran-2,6'-cyclohexene]-6-yl] trifluoromethanesulfonate (20 g) was dissolved in toluene (200 mL). To this, palladium acetate (II) (0.477)), 4,5-bis(diphenylphosphino)-9,9-dimethylxanthene (2.46 g) and N,N-diisopropylethylamine (14.8 mL) were added. The reaction mixture was heated to 80° C.

2,4,6-Trichlorophenyl formate (12.5 g) was divided into three portions, which were added at intervals of 30 minutes to the reaction mixture.

After the reaction mixture was stirred at 80° C. for 30 minutes, the reaction mixture was poured into water and extracted with ethyl acetate. The organic layer was washed with water and saturated saline and (tried over anhydrous sodium sulfate. The solvent was distilled away under reduced pressure and the resultant residue was purified by silica gel column chromatography [elution solvent: n-hexane/ethyl acetate=7/3–3/7 (V/V)] to obtain the title compound (19.5 g (yield: 84%)) as a white solid.

5b (2S,5'R)—N'-Acetyl-7-chloro-1',4-dimethoxy-5'-methyl-3,3'-dioxo-spiro[benzofuran-2,6'-cyclohexene]-6-carbohydrazide The compound of Example 5 (5a): 2,4,6-trichlorophenyl) (2S,5'R)-7-chloro-1',4-dimethoxy-5'-methyl-3,3'-dioxo-spiro[benzofuran-2,6'-cyclohexene]-6-carboxylate (3.5 g) was dissolved in dichloromethane (400 mL). To this, 3H-1,2,3-triazolo[4,5-b]pyridin-3-ol (8.72 g), acetohydrazide (purity: 90%, 7.12 g), 4-dimethylaminopyridine (0.783 g) and triethylamine (26.8 mL) were added. The reaction solution was allowed to stand still at room temperature overnight.

The reaction solution was washed with water and saturated saline and dried over anhydrous sodium sulfate. The solvent was distilled away under reduced pressure and the resultant residue was purified by silica gel column chromatography [elution solvent: methanol/ethyl acetate=0/10–1/9 (V/V)] to obtain the title compound (23.4 g (yield: 86%)) as a white solid.

5c (2S,5'R)-7-Chloro-3',4-dimethoxy-5'-methyl-6-(5-methyl-1,3,4-oxadiazol-2-yl)spiro[benzofuran-2,4'-cyclohex-2-ene]-1',3-dione The compound of Example 5 (5b) (2S,5'R)—N'-acetyl-7-chloro-1',4-dimethoxy-5'-methyl-3,3'-dioxo-spiro[benzofuran-2,6'-cyclohexene]-6-carbohydrazide (0.25 g) was dissolved in toluene (5 mL) and anhydrous 1,4-dioxane (5 mL). To this, a (methoxycarbonylsulfamoyl)triethylammonium hydroxide inner salt (0.169 g) was added. The reaction mixture was stirred at 60° C. for one hour.

To the reaction mixture, water was added. The reaction mixture was extracted with ethyl acetate. The organic layer was washed with saturated saline and dried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (49 mg (yield: 20%)) as a white solid.

Example 6

(2S,5'R)-7-Chloro-3',4-dimethoxy-5'-methyl-6-(3-methyl-1,2,4-oxadiazol-5-yl)spiro[benzofuran-2,4'-cyclohex-2-ene]-1',3-dione 6a

[(Z)-1-Aminoethylideneamino] (2S,5'R)-7-chloro-1',4-dimethoxy-5'-methyl-3,3'-dioxo-spiro[benzofuran-2,6'-cyclohexene]-6-carboxylate The compound of Example 5 (5a): (2,4,6-trichlorophenyl) (2S,5'R)-7-chloro-1',4-dimethoxy-5'-methyl-3,3'-dioxo-spiro[benzofuran-2,6'-cyclohexene]-6-carboxylate (3 g) was dissolved in dichloromethane (50 mL). To this, N'-hydroxyethanimidamide (0.488 g), 3H-1,2,3-triazolo[4,5-b]pyridin-3-ol (0.748 g), 4-dimethylaminopyridine (0.0671 g) and triethylamine (2.28 mL) were added. The reaction solution was allowed to stand still at room temperature overnight.

The reaction solution was diluted with ethyl acetate and the organic layer was washed with water and saturated saline and dried over anhydrous sodium sulfate. The solvent was distilled away under reduced pressure and the resultant residue was purified by silica gel column chromatography [elution solvent: n-hexane/ethyl acetate=80/20–0/100 (V/V)] to obtain the title compound (2.32 g (yield: quantitative)) as a white solid.

6b (2S,5'R)-7-Chloro-3',4-dimethoxy-5'-methyl-6-(3-methyl-1-1,2,4-oxadiazol-5-yl)spiro[benzofuran-2,4'-cyclohex-2-ene]-1',3-dione The compound of Example 6 (6a): [(Z)-1-aminoethylideneamino] (2S,5'R)-7-chloro-1',4-dimethoxy-5'-methyl-3,3'-dioxo-spiro[benzofuran-2,6'-cyclohexene]-6-carboxylate (0.95 g) was dissolved in toluene (20 mL). The reaction solution was stirred at 110° C. for 6 hours and concentrated. The resultant residue was parified by silica gel column chromatography [elution solvent: n-hexane/ethyl acetate=8/2–3/7 (V/V)] and triturated with n-hexane and ethyl acetate to obtain the title compound (756 mg (yield: 83%)) as a white solid.

Example 7

(2S,5'R)-7-Chloro-3',4-dimethoxy-5'-methyl-6-(5-methyl-1,2,4-oxadiazol-3-yl)spiro[benzofuran-2,4'-cyclohex-2-ene]-1',3-dione 7a (2S,5'R)-7-Chloro-3',4-dimethoxy-5'-methyl-3,3'-dioxo-spiro[benzofuran-2,6'-cyclohexene]-6-carbonitrile The compound of Example 3 (3a): [(2S,5'R)-7-chloro-1',4-dimethoxy-5'-methyl-3,3'-dioxo-spiro[benzofuran-2,6'-cyclohexene]-6-yl] trifluoramethanesulfonate (1 g) was dissolved in N,N-dimethylformamide (10 mL). To this, tetrakis(triphenylphosphine)palladium (0) (0.245 g) and zinc cyanide (0.499 g) were added. The reaction mixture was stirred at 90° C. for 5 hours.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=8/2–3/7 (V/V)] to obtain the title compound (540 mg (yield: 73%)) as a light yellow solid.

7b (2S,5'R)-7-Chloro-3',4-dimethoxy-5'-methyl-6-(5-methyl-1,2,4-oxadiazol-3-yl)spiro[benzofuran-2,4'-cyclohex-2-ene]-1',3-dione The compound of Example 7 (7a): (2S,5'R)-7-chloro-1',4-dimethoxy-5'-methyl-3,3'-dioxo-spiro[benzofuran-2,6'-cyclohexene]-6-carbonitrile (0.54 g) was dissolved in ethanol (10 mL). To this, 50% hydroxylamine solution (0.19 mm) was added. The reaction solution was stirred at 90° C. for 6 hours.

The reaction solution was concentrated and subjected to azeotropic twice with toluene. The residue was dissolved in dichloromethane (20 mL). To this, acetic acid (0.0891 mL), 1-ethyl-3-(3-dimethylaminopropyl) carbodiimide hydrochloride (0.299 g), 3H-1,2,3-triazolo[4,5-b]pyridin-3-ol (0.0424 g) and triethylamine (0.652 mL) were added. The reaction solution was stirred at room temperature for 5 hours.

The reaction solution was diluted with dichloromethane and the organic layer was washed with water and saturated saline and dried over anhydrous sodium sulfate. The solvent was distilled away under reduced pressure and the resultant residue was roughly purified by silica gel column chromatography [elution solvent: n-hexane/ethyl acetate=1/1–0/1 (V/V)]. The resultant crude product was suspended in tolune (5 mL) and the suspension solution was stirred at 100° C. for 7 hours.

To the reaction mixture, water was added, and the reaction mixture was extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=7/3–2/8 (V/V)] to obtain the title compound (34 mg (yield: 5.4%, 3 steps)) as a white solid.

Example 8

(2S,5'R)-7-Chloro-6-[5-(1-hydroxy-1-methyl-ethyl)-1,3,4-oxadiazol-2-yl]-3',4-dimethoxy-5'-methyl-spiro[benzofuran-2,4'-cyclohex-2-ene]-1',3-dione 8a (2S,5'R)-7-Chloro-N'-(2-hydroxy-2-methyl-propanoyl)-1',4-dimethoxy-5'-methyl-3,3'-dioxo-spiro[benzofuran-2,6'-cyclohexene]-6-carbohydrazide The compound of Example 5 (5a): 2,4,6-trichlorophenyl) (2S,5'R)-7-chloro-1',4-dimethoxy-5'-methyl-3,3'-dioxo-spiro[benzofuran-2,6'-cyclohexene]-6-carboxylate (0.5 g)

was dissolved in dichloromethane (10 mL). To this, 2-hydroxy-2-methylpropanohydrazide (0.162 g), 3H-1,2,3-triazolo[4,5-b]pyridin-3-ol (0.125 g), 4-dimethylaminopyridine (0.0224 g) and triethylamine (0.639 mL) were added. The reaction mixture was allowed to stand still at room temperature overnight.

The solvent was distilled away under reduced pressure and the resultant residue was purified by silica gel column chromatography [elution solvent: methanol/ethyl acetate=0/10–1/9 (V/V)] to obtain the title compound (415 mg (yield: 97%)) as a white solid.

8b (2S,5'R)-7-Chloro-6-[5-(1-hydro-1-methyl-ethyl)-1,3,4-oxadiazol-2-yl]-3',4-dimethoxy-5'-methyl-spiro[benzofuran-2,4'-cyclohex-2-ene]-1',3-dione The compound of Example 8 (8a): (2S,5'R)-7-chloro-N'-(2-hydroxy-2-methyl-propanoyl)-1',4-dimethoxy-5'-methyl-3,3'-dioxo-spiro[benzofuran-2,6'-cyclohexene]-6-carbohydrazide (0.415 g) was dissolved in dichloromethane (5 mL). To this, triethylamine (0.62 mL) and p-toluenesulfonyl chloride (0.254)) were added. The reaction mixture was stirred at room temperature for two hours.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: methanol/ethyl acetate=0/10–1/9 (V/V)] to obtain the title compound (141 mg (yield: 35%)) as a white solid.

Example 9

(2S,5'R)-7-Chloro-6-[5-[(1S)-1-hyroxyethyl]-1,3,4-oxadiazol-2-yl]-3',4-dimethoxy-5'-methyl-spiro[benzofuran-2,4'-cyclohex-2-ene]-1',3-dione 9a (2S)-2-Tetrahydropyran-2-yloxypropanehydrazide Methyl (2S)-2-tetrahydropyran-2-yloxypropanoate (CAS Registry Number: 158829-63-1, J. Ora. Chem. 1991, 56, 1086-1093) (2.2 g) was dissolved in ethanol (8 mL). To this, hydrazine monohydrate (1.8 g) was added. The reaction mixture was allowed to stand still at room temperature overnight. The solvent was distilled away under reduced pressure and the resultant residue was purified by silica gel column chromatography [elution solvent: methanol/ethyl acetate=0/10–1/9 (V/V)] to obtain the title compound (1.6 g (yield: 73%)) as a white solid.

9b (2S,5'R)-7-Chloro-1',4-dimethoxy-5'-methyl-3,3'-dioxo-N'-[(2S)-2-tetrahydropyran-2-yloxypropanoyl]spiro[benzofuran-2,6'-cyclohexene]-6-carbohydrazide The compound of Example 5 (5a): (2,4,6-trichlorophenyl) (2S,5'R)-7-chloro-1',4-dimethoxy-5'-methyl-3,3'-dioxo-spiro[benzofuran-2,6'-cyclohexene]-6-carboxylate (0.5 g) was dissolved in dichloromethane (10 mL). To this, the compound of Example 9 (9a): (2S)-2-tetrahydropyran-2-yloxypropanehydrazide (0.258 g), 3H-1,2,3-triazolo[4,5-b]pyridin-3-ol (0.125 g), 4-dimethylaminopyridine (0.0112 g) and N,N-diisopropylethylamine (0.478 mL) were added. The reaction mixture was allowed to stand still at room temperature overnight.

The reaction mixture was poured into water, neutralized with 1 mol/l hydrochloric acid and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (490 mg (yield: quantitative)) as a white solid.

9c (2S,5'R)-7-Chloro-3',4-dimethoxy-5'-methyl-6-[5-[(1S)-1-tetrahydropyran-2-yloxyethyl]-1,3,4-oxadiazol-2-yl]spiro[benzofuran-2,4'-cyclohex-2-ene]-1',3-dione The compound of Example 9 (9b): (2S,5'R)-7-chloro-1',4-dimethoxy-5'-methyl-3,3'-dioxo-N'-[(2S)-2-tetrahydropyran-2-yloxypropanoyl]spiro[benzofuran-2,6'-cyclohexene]-6-carbohydrazide (0.49 g) was dissolved in dichloromethane (5 mL). To this, triethylamine (0.637 ml) and p-toluenesulfonyl chloride (0.209 g) were added. The reaction mixture was stirred at room temperature for three hours.

The reaction mixture was poured into water, neutralized with 1 mol/l hydrochloric acid and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (452 mg (yield: 95%)) as a white solid.

9d (2S,5'R)-7-Chloro-6-[5-[(1S)-1-hydroxyethyl]-1,3,4-oxadiazol-2-yl]-3',4-dimethoxy-5'-methyl-spiro[benzofuran-2,4'-cyclohex-2-ene]-1',3-dione The compound of Example 9 (9c): (2S,5'R)-7-chloro-3',4-dimethoxy-5'-methyl-6-[5-[(1S)-1-tetrahydropyran-2-yloxyethyl]-1,3,4-oxadiazol-2-yl]spiro[benzofuran-2,4'-cyclohex-2-ene]-1',3-dione (0.452 g) was dissolved in ethanol (4 mL). To this, water (1 mL) and p-toluenesulfonic acid monohydrate (0.0828 g) were added. The reaction mixture was stirred at 50° C. for one hour.

The reaction mixture was poured into water and 1 mol/l hydrochloric acid was added thereto. The reaction mixture was extracted with ethyl acetate. The organic layer was washed with water and saturated saline and dried over anhydrous sodium sulfate. The solvent was distilled away under reduced pressure and the resultant residue was purified by silica gel column chromatography [elution solvent: methanol/ethyl acetate=0/1–1/19 (V/V)] to obtain the title compound (119 mg (yield: 31%)) as a white solid.

Example 10

(2S,5'R)-7-Chloro-6-[5-[(1R)-1-hydroxyethyl]-1,3,4-oxadiazol-2-yl]-3',4-dimethoxy-5'-methyl-spiro[benzofuran-2,4'-cyclohex-2-ene]-1',3-dione

10a (2R)-2-Tetrahydropyran-2-yloxypropanehydrazide

Methyl (2R)-2-tetrahydropyran-2-yloxypropanoate (CAS Registry Number: 124508-74-3, Tetrahedron, 2012, 68, 7068-2073) (1.6)) was dissolved in ethanol (8 mL). To this, hydrazine monohydrate (1.2 mL) was added. The reaction mixture was stirred at 90° C. for 4 hours.

After the reaction mixture was allowed to stand still at room temperature overnight, the mixture was stirred at 90° C. for 10 hours. The mixture was further allowed to stand at room temperature overnight and then stirred at 90° C. for 10 hours. The solvent was distilled away under reduced pressure and the resultant residue was purified by silica gel column chromatography [elution solvent: methanol/ethyl acetate=0/1-1/9 (V/V)] to obtain the title compound (1 g (yield: 62%)) as a white solid.

10b (2S,5'R)-7-Chloro-1',4-dimethoxy-5'-methyl-3,3'-dioxo-N'-[(2R)-2-tetrahydropyran-2-yloxypropanoyl]spiro[benzofuran-2,6'-cyclohexene]-6-carbohydrazide The compound of Example 5 (5a): (2,4,6-trichlorophenyl) (2S,5'R)-7-chloro-1',4-dimethoxy-5'-methyl-3,3'-dioxospiro[benzofuran-2,6'-cyclohexene]-6-carboxylate (0.5 g) was dissolved in dichloromethane (10 mL). To this, the compound of Example 10 (10a): (2R)-2-tetrahydropyran-2-yloxypropanehydrazide (0.19 g), 3H-1,2,3-triazolo[4,5-b]pyridin-3-ol (0.124 g), 4-dimethylaminopyridine (0.0112 g) and N,N-diisopropylethylamine (0.478 mL) were added. The reaction mixture was allowed to stand still at room temperature overnight.

The reaction mixture was poured into water, neutralized with 1 mol/l hydrochloric acid and extracted with ethyl acetate. The organic layer was washed with water and saturated saline and dried over anhydrous sodium sulfate. The solvent was distilled away under reduced pressure and the resultant residue was purified by silica gel column chromatography [elution solvent: methanol/ethyl acetate=0/10-1/9 (V/V)] to obtain the title compound (460 mg (yield: 94%)) as a white solid.

10c (2S,5'R)-7-Chloro-3',4-dimethoxy-5'-methyl-6-[5-[(1R)-1-tetrahydropyran-2-yloxyethyl]-1,3,4-oxadiazol-2-yl]spiro[benzofuran-2,4'-cyclohex-2-ene]-1',3-dione The compound of Example 10 (10b): (2S,5'R)-7-chloro-1',4-dimethoxy-5'-methyl-3,3'-dioxo-N'-[(2R)-2-tetranydropyran-2-yloxypropanoyl]spiro[benzofuran-2,6'-cyclohexene]-6-carbohydrazide (0.46 g) was dissolved in dichloromethane (5 mL). To this, triethylamine (0.598 mL) and p-toluenesulfonyl chloride (0.196 g) were added. The reaction mixture was stirred at room temperature for two hours.

The reaction mixture was poured into water, neutralized with 1 mol/l hydrochloric acid and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (315 mg (yield: 71%)) as a white solid.

10d (2S,5'R)-7-Chloro-6-[5-[(1R)-1-hydroxyethyl]-1,3,4-oxadiazol-2-yl]-3',4-dimethoxy-5'-methyl-spiro[benzofuran-2,4'-cyclohex-2-ene]-1',3-dione The compound of Example 10 (10c): (2S,5'R)-7-chloro-3',4-dimethoxy-5'-methyl-6-[5-[(1R)-1-tetrahydropyran-2-yloxyethyl]-1,3,4-oxadiazol-2-yl]spiro[benzofuran-2,4'-cyclohex-2-ene]-1',3-dione (0.315 g) was dissolved in ethanol (4 mL). To this, water (1 mL) and p-toluenesulfonic acid monohydrate (0.0577 g) were added. The reaction mixture was stirred at 50° C. for one hour.

The reaction mixture was poured into water and 1 mol/l hydrochloric acid was added thereto. The reaction mixture was extracted with ethyl acetate. The organic layer was washed with water and saturated saline and dried over anhydrous sodium sulfate. The solvent was distilled away under reduced pressure and the resultant residue was purified by silica gel column chromatography [elution solvent: methanol/ethyl acetate=0/10–1/19 (V/V)] to obtain the title compound (112 mg (yield: 42%)) as a white solid.

Example 11

(2S,5'R)-7-Chloro-4-ethoxy-6-[5-(1-hydroxy-1-methyl-ethyl)-1,3,4-oxadiazol-2-yl]-3'-methoxy-5'-methyl-spiro[benzofuran-2,4'-cyclohex-2-ene]-1',3-dione

11a (2S,5'R)-7-Chloro-4-hydroxy-6-[5-(1-hydroxy-1-methyl-ethyl)-1,3,4-oxadiazol-2-yl]-3'-methoxy-5'-methyl-spiro[benzofuran-2,4'-cyclohex-2-ene]-1',3-dione Magnesium chips (0.41 g) were added in diethyl ether (60 mL) and iodine (3.9 g) was divided into three portions, which were added at intervals of 20 minutes. The reaction mixture was stirred at room temperature for one hour, and then, the compound of Example 8 (8b): (2S,5'R)-7-chloro-6-[5-(1-hydroxy-1-methyl-ethyl)-1,3,4-oxadiazol-2-yl]-3',4-dimethoxy-5'-methyl-spiro[benzofuran-2,4'-cyclohex-2-ene]-1',3-dione (6.3 g) and toluene (150 mL) were added thereto. The reaction mixture was stirred at 90° C. for 7 hours.

To the reaction mixture, water was added. The mixture was neutralized with 1 mol/l hydrochloric acid, and then, made slightly alkaline by adding saturated aqueous sodium bicarbonate. The reaction mixture was extracted with ethyl acetate. The organic layer was washed with 1 mol/l hydrochloric acid and saturated saline and dried over anhydrous sodium sulfate. The solvent was distilled away under reduced pressure and the resultant residue was purified by silica gel column chromatography [elution solvent:

n-hexane/ethyl acetate=1/1–0/1 (V/V)] to obtain the title compound (2.7 g (yield: 44%)) as a white solid.

11b (2S,5'R)-7-Chloro-4-ethoxy-6-[5-(1-hydroxy-1-methyl-ethyl)-1,3,4-oxadiazol-2-yl]-3'-methoxy-5'-methyl-spiro[benzofuran-2,4'-cyclohex-2-ene]-1',3-dione The compound of Example 11 (11a): (2S,5'R)-7-chloro-4-hydroxy-6-[5-(1-hydroxy-1-methyl-ethyl)-1,3,4-oxadiazol-2-yl]-3'-methoxy-5'-methyl-spiro[benzofuran-2,4'-cyclohex-2-ene]-1',3-dione (0.3 g) was dissolved in N,N-dimethylformamide (4 mL). To this, potassium carbonate (0.191)) and iodoethane (0.0827 mL) were added. The reaction mixture was stirred at 80° C. for two hours.

The reaction mixture was poured into water, neutralized with 1 mol/l hydrochloric acid and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=6/4–1/9 (V/V)] to obtain the title compound (42 mg (yield: 13%)) as a white solid.

Example 12

(2S,5'R)-7-Chloro-4-ethoxy-6-[5-[(1S)-1-hydroxy-ethyl]-1,3,4-oxadiazol-2-yl]-3'-methoxy-5'-methyl-spiro[benzofuran-2,4'-cyclohex-2-ene]-1',3-dione Magnesium chips (0.073 g) were added in diethyl ether (20 mL) and a small amount of iodine (0.70 g) was added thereto. The reaction mixture was stirred at room temperature for 10 minutes. Further, iodine (0.70 g) was divided into three portions, which were added at intervals of 20 minutes. After the reaction mixture was stirred at room temperature for 30 minutes, toluene (50 mL), the compound of Example 9 (9c): (2S,5'R)-7-chloro-3',4-dimethoxy-5'-methyl-6-[5-[(1S)-1-tetrahydropyran-2-yloxyethyl]-1,3,4-oxadiazol-2-yl]spiro[benzofuran-2,4'-cyclohex-2-ene]-1',3-dione (1.3 g) were added thereto. The reaction mixture was stirred at 80° C. for 8 hours.

To the reaction mixture, water was added. The mixture was neutralized with 1 mol/l hydrochloric acid and extracted with ethyl acetate. The organic layer was washed with saturated saline and dried over anhydrous sodium sulfate.

The solvent was distilled off under reduced pressure and the resultant residue was dissolved in N,N-dimethylformamide (10 mL). To this, potassium carbonate (1.36 g) and iodoethane (0.485 were added. The reaction mixture was stirred at 80° C. for one hour. The reaction mixture was poured into water, neutralized with 1 mol/l hydrochloric acid and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=7/3–2/8 (V/V)]. The solid obtained was triturated with n-hexane and ethyl acetate to obtain the title compound (122 mg (yield: 13%)) as a white solid.

Example 13

(2S,5'R)-7-Chloro-6-[3-(1-hydroxyethyl)-1,2,4-oxadiazol-5-yl]-3',4-dimethoxy-5'-methyl-spiro[benzofuran-2,4'-cyclohex-2-ene]-1',3-dione 13a 2-Tetrahydropyran-2-yloxypropanenitrile 2-Hydroxypropanenitrile (5.0 g) was dissolved in dichloromethane (150 mL). To this, 3,4-dihydro-2H-pyran (7.7 g) and p-toluenesulfonic acid monohydrate (1.3 g) were added. The reaction solution was stirred at room temperature for 14 hours. To the reaction solution, triethylamine was added, and then, the solvent was distilled off under reduced pressure. The resultant residue was purified by silica gel column chromatography [elution solvent: n-hexane/ethyl acetate=97/3–7/3 (V/V)] to obtain the title compound, more specifically, two types of diastereomer (5.7 g (yield: 52%) and 2.5 g (yield: 23%), respectively) as light yellow solids.

13b

N'-Hydroxy-2-tetrahydropyran-2-yloxy-propanamidine

One of the diastereomers obtained in Example 13 (13a): 2-tetrahydropyran-2-yloxypropanenitrile (5.6 g) was dissolved in ethanol (36 mL). To this, a 50% hydroxylamine solution (4.3 mL) was added. The reaction mixture was heated to 80° C. and stirred for 5 hours. After the temperature of the reaction mixture had returned to room temperature, the solvent was distilled off under reduced pressure. The resultant residue was purified by silica gel column chromatography [elution solvent: n-hexane/ethyl acetate=10/1–1/0 (V/V)] to obtain the title compound (5.0 g (yield: 74%) as a light yellow solid.

13c

[(Z)-(1-Amino-2-tetrahydropyran-2-yloxy-propylidene)amino] (2S,5'R)-7-chloro-1',4-dimethoxy-5'-methyl-3,3'-dioxo-spiro[benzofuran-2,6'-cyclohex-ene]-6-carboxylate The compound of Example 5 (5a): (2,4,6-trichlorophenyl) (2S,5'R)-7-chloro-1',4-dimethoxy-5'-methyl-3,3T-dioxo-spiro[benzofuran-2,6'-cyclohexene]-6-carboxylate (0.5 g) was dissolved in dichloromethane (10 mL). To this, the compound of Example 13 (13b): hydroxy-2-tetrahydropyran-2-yloxy-propanamidine (0.207 g), 3H-1,2,3-triazolo[4,5-b]pyridin-3-ol (0.125 g), 4-dimethylaminopyridine (0.0112 g) and N,N-diisopropylethylamine (0.478 mL) were added. The reaction mixture was stirred at room temperature for 5 hours.

The reaction mixture was poured into water, neutralized with 1 mol/l hydrochloric acid and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (410 mg (yield: 83%)) as a white solid.

13d (2S,5'R)-7-Chloro-3',4-dimethoxy-5'-methyl-6-[3-(1-tetrahydropyran-2-yloxyethyl)-1,2,4-oxadiazol-5-yl]spiro[benzofuran-2,4'-cyclohex-2-ene]-1',3-dione The compound of Example 13 (13c): [(Z)-(1-amino-2-tetrahydropyran-2-yloxy-propylidene)amino] (2S,5'R)-7-chloro-1',4-dimethoxy-5'-methyl-3,3'-dioxo-spiro[benzofuran-2,6'-cyclohexene]-6-carboxylate (0.41 g) was dissolved in toluene (5 mL). The reaction mixture was stirred at 110° C. for 7 hours. The solvent was distilled away under reduced pressure and the resultant residue was purified by silica gel column chromatography [elution solvent: n-hexane/ethyl acetate=1/1–1/9 (V/V)] to obtain the title compound. (375 mg (yield: 95%)) as a white solid.

13e (2S,5'R)-7-Chloro-6-[3-(1-hydroxyethyl)-1,2,4-oxadiazol-5-yl]-3',4-dimethoxy-5'-methyl-spiro[benzofuran-2,4'-cyclohex-2-ene]-1',3-dione The compound of Example 13 (13d) (2S,5'R)-7-chloro-3',4-dimethoxy-5'-methyl-6-[3-(1-tetrahydropyran-2-yloxyethyl)-1,2,4-oxadiazol-5-yl]spiro[benzofuran-2,4'-cyclohex-2-ene]-1',3-dione (0.375 g) was dissolved in ethanol (4 mL). To this, p-toluenesulfonic acid monohydrate (0.0687 g) and water (1 mL) were added. The reaction mixture was stirred at room temperature for 8 hours.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (195 mg (yield: 62%)) as a white solid.

Example 14

(2S,5'R)-7-Chloro-4-(2-hydroxyethoxy)-3'-methoxy-5'-methyl-6-(5-methyl-1,3,4-oxadiazol-2-yl)spiro[benzofuran-2,4'-cyclohex-2-ene]-1',3-dione

14a (2S,5'R)-7-Chloro-4-hydroxy-3',6-dimethoxy-5'-methyl-spiro[benzofuran-2,4'-cyclohex-2-ene]-1',3-dione Magnesium chips (1.03 g) were added in diethyl ether (50 mL) and iodine (8.63 g) was added thereto little by little over one hour. After the reaction mixture was stirred at room temperature for 30 minutes, toluene (100 mL) and (+)-griseofulvin (10 g) were added thereto. The reaction mixture was stirred at 80° C. for three hours.

To the reaction mixture, water was added. The mixture was neutralized with 1 mol/l hydrochloric acid and extracted with ethyl acetate. The organic layer was washed with a saturated saline and dried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (7.8 g (yield: 81%)) as a white solid.

14b (2S,5'R)-7-Chloro-3',6-dimethoxy-5'-methyl-4-(2-tetrahydropyran-2-yloxyethoxy)spiro[benzofuran-2,4'-cyclohex-2-ene]-1',3-dione The compound of Example 14 (14a): (2S,5'R)-7-chloro-4-hydroxy-3',6-dimethoxy-5'-methyl-spiro[benzofuran-2,4'-cyclohex-2-ene]-1',3-dione (5.1 g) was dissolved in N,N-dimethylformamide (60 mL). To this, 2-(2-bromoethoxy)tetrahydro-2H-pyran (3.8 g) and potassium carbonate (6.2 g) were added. The reaction mixture was stirred at 80° C. for 7 hours.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=8/2–3/7 (V/V)] to obtain the title compound (6.9 g (yield: 98%)) as a white solid.

14c (2S,5'R)-7-Chloro-6-hydroxy-3'-methoxy-5'-methyl-4-(2-tetrahydropyran-2-yloxyethoxy)spiro[benzofuran-2,4'-cyclohex-2-ene]-1',3-dione The compound of Example 14 (14b): (2S,5'R)-7-chloro-3',6-dimethoxy-5'-methyl-4-(2-tetrahydropyran-2-yloxyethoxy)spiro[benzofuran-2,4'-cyclohex-2-ene]-1',3-dione (6.9 g) was dissolved in pyridine (70 mL). To this, 18-crown-6-ether (4.3 g) and potassium iodide (2.5 g) were added. The reaction mixture was stirred at 120° C. for 8 hours.

The reaction solution was concentrated and the reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (3.8 g (yield: 57%)) as a white solid.

14d

[(2S,5'R)-7-Chloro-1'-methoxy-5'-methyl-3,3'-dioxo-4-(2-tetrahydropyran-2-yloxyethoxy)spiro[benzofuran-2,6'-cyclohexene]-6-yl] trifluoromethanesulfonate The compound of Example 14 (14c): (2S,5'R)-7-chloro-6-hydroxy-3'-methoxy-5'-methyl-4-(2-tetrahydropyran-2-yloxyethoxy)spirobenzofuran-2,4'-cyclohexa-2-ene]-1',3-dione (3.8 g) was dissolved in dichloromethane (40 mL). To this, triethylamine (2.9 mL) and N-phenylbis(trifluoromethanesulfonimide) (3.6 g) were added. The reaction mixture was allowed to stand still at room temperature overnight.

The reaction solution was diluted with dichloromethane. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=8/2–4/6 (V/V)] to obtain the title compound (3.2 g (yield: 65%)) as a white solid.

14e (2,4,6-Trichlorophenyl) (2S,5'R)-7-chloro-1'-methoxy-5'-methyl-3,3'-dioxo-4-(2-tetrahydropyran-2-yloxyethoxy)spiro[benzofuran-2,6'-cyclohexene]-6-carboxylate The compound of Example 14 (14d): [(2S,5'R)-7-chloro-1-methoxy-5'-methyl-3,3'-dioxo-4-(2-tetrahydropyran-2-yloxyethoxy)spiro[benzofuran-2,6'-cyclohexene]-6-yl] trifluoromethanesulfonate (1 g) was dissolved in toluene (200 mL). To this, palladium acetate (II) (0.0192 g), 4,5-bis (diphenylphosphino)-9,9-dimethylxanthene (0.0989 g) and N,N-diisopropylethylamine (0.596 mL) were added. The reaction mixture was heated to 80° C.

2,4,6-Trichlorophenyl formate (0.501 g) was divided into three portions, which were added at intervals of 10 minutes. The reaction mixture was stirred at 80° C. for 30 minutes, and then, the temperature of the mixture was returned to room temperature. The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=8/2–4/6 (V/V)] to obtain the title compound (850 mg (yield: 75%)) as a white solid.

14f (2S,5'R)—N'-Acetyl-7-chloro-1'-methoxy-5'-methyl-3,3'-dioxo-4-(2-tetrahydropyran-2-yloxyethoxy)spiro[benzofuran-2,6'-cyclohexene]-6-carbohydrazide The compound of Example 14 (14e): (2,4,6-trichlorophenyl) (2S,5'R)-7-chloro-1'-methoxy-5'-methyl-3,3'-dioxo-4-(2-tetrahydropyran-2-yloxyethoxy)spiro[benzofuran-2,6'-cyclohexene]-6-carboxylate (0.4 g) was dissolved in dichloromethane (20 mL). To this, acetohydrazide (purity: 90%, 0.0673 g), 3H-1,2,3-triazolo[4,5-b]pyridin-3-ol (0.0824 g), 4-dimethylaminopyridine (0.0148 g) and triethylamine (0.254 mL) were added. The reaction mixture was allowed to stand still at room temperature overnight.

The reaction mixture was poured into water, neutralized with 1 mol/l hydrochloric acid and extracted with ethyl acetate. The organic layer was washed with water and saturated saline and dried over anhydrous sodium sulfate. The solvent was distilled away under reduced pressure and the resultant residue was purified by silica gel column chromatography [elution solvent: methanol/ethyl acetate=0/10–1/9 (V/V)] to obtain the title compound. (280 mg (yield: 86%)) as a white solid.

14g (2S,5'R)-7-Chloro-3'-methoxy-5'-methyl-6-(5-methyl-1,3,4-oxadiazol-2-yl)-4-(2-tetrahydropyran-2-yloxyethoxy)spiro[benzofuran-2,4'-cyclohex-2-ene]-1',3-dione The compound of Example 14 (14f): (2S,5'R)—N'-acetyl-7-chloro-1'-methoxy-5'-methyl-3,3'-dioxo-4-(2-tetrahydropyran-2-yloxyethoxy)spiro[benzofuran-2,6'-cyclohexene]-6-carbohydrazide (0.28 g) was dissolved in dichloromethane (5 mL). To this, p-toluenesulfonyl chloride (0.149 g) and triethylamine (0.364 mL) were added. The reaction mixture was stirred at room temperature for three hours.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: n-hexane/ethyl acetate=1/1–0/1 (V/V)] to obtain the title compound (202 mg (yield: 75%)) as a white solid.

14h (2S,5'R)-7-Chloro-4-(2-hydroxyethoxy)-3'-methoxy-5'-methyl-6-(5-methyl-1,3,4-oxadiazol-2-yl)spiro[benzofuran-2,4'-cyclohex-2-ene]-1',3-dione The compound of Example 14 (14g): (2S,5'R)-7-chloro-3'-methoxy-5'-methyl-6-(5-methyl-1,3,4-oxadiazol-2-yl)-4-(2-tetrahydropyran-2-yloxyethoxy)spiro[benzofuran-2,4'-cyclohex-2-ene]-1',3-dione (0.202 g) was dissolved in ethanol (2 mL). To this, p-toluenesulfonic acid monohydrate (0.037 g) and water (5 mL) were added. The reaction mixture was stirred at 50° C. for two hours.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: methanol/ethyl acetate=0/10–1/9 (V/V)] to obtain the title compound (39 mg (yield: 23%)) as a white solid.

Example 15

(2S,5'R)-7-Chloro-4-(2-hydroxyethoxy)-3'-methoxy-5'-methyl-6-(3-methyl-1,2,4-oxadiazol-5-yl)spiro[benzofuran-2,4'-cyclohex-2-ene]-1',3-dione 15a

[(Z)-1-Aminoethylideneamino] (2S,5'R)-7-chloro-1'-methoxy-5'-methyl-3,3'-dioxo-4-(2-tetrahydropyran-2-yloxyethoxy)spiro[benzofuran-2,6'-cyclohexene]-6-carboxylate The compound of Example 14 (14e) (2,4,6-trichlorophenyl) (2S,5'R)-7-chloro-1'-methoxy-5'-methyl-3,3'-dioxo-4-(2-tetrahydropyran-2-yloxyethoxy)spiro[benzofuran-2,6'-cyclohexene]-6-carboxylate (0.45 g) was dissolved in dichloromethane (10 mL). To this, N'-hydroxyethanimidamide (0.0758 g), 3H-1,2,3-triazolo[4,5-b]pyridin-3-ol (0.0928 g), 4-dimethylaminopyridine (0.00833 g) and triethylamine (0.285 mL) were added. The reaction mixture was allowed to stand still at room temperature overnight.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: methanol/ethyl acetate=0/10–1/9 (V/V)] to obtain the title compound (345 mg (yield: 94%)) as a white solid.

15b (2S,5'R)-7-Chloro-3'-methoxy-5'-methyl-6-(3-methyl-1,2,4-oxadiazol-5-yl)-4-(2-tetrahydropyran-2-yloxyethoxy)spiro[benzofuran-2,4'-cyclohex-2-ene]-1',3-dione The compound of Example 15 (15a): [(Z)-1-aminoethylideneamino] (2S,5'R)-7-chloro-1'-methoxy-5'-methyl-3,3'-dioxo-4-(2-tetrahydropyran-2-yloxyethoxy)spiro[benzofuran-2,6'-cyclohexene]-6-carboxylate (0.345 g) was suspended in toluene (5 mL). The reaction mixture was stirred at 100° C. for 5 hours. The solvent was distilled away under reduced pressure and the resultant residue was purified by silica gel column chromatography [elution solvent: n-hexane/ethyl acetate=1/1–0/1 (V/V)] to obtain the title compound (283 mg (yield: 85%)) as a white solid.

15c (2S,5'R)-7-Chloro-4-(2-hydroxyethoxy)-3'-methoxy-5'-methyl-6-(3-methyl-1,2,4-oxadiazol-5-yl)spiro[benzofuran-2,4'-cyclohex-2-ene]-1',3-dione The compound of Example 15 (15b): (2S,5'R)-7-chloro-3'-methoxy-5'-methyl-6-(3-methyl-1,2,4-oxadiazol-5-yl)-4-(2-tetrahydropyran-2-yloxyethoxy)spiro[benzofuran-2,4'-cyclohex-2-ene]-1',3-dione (0.283 g) was dissolved in ethanol (2 mL). To this, p-toluenesulfonic acid monohydrate (0.0518 g) and water (5 mL) were added. The reaction mixture was stirred at 50° C. for three hours.

The reaction mixture was poured into water and extracted with ethyl acetate. The organic layer was washed with water and saturated saline and dried over anhydrous sodium sulfate. The solvent was distilled away under reduced pressure and the resultant residue was purified by silica gel column chromatography [elution solvent: methanol/ethyl acetate=0/10–1/9 (V/V)] to obtain the title compound (128 mg (yield: 54%)) as a white solid.

Example 16

(2S,5'R)-7-Chloro-4-(2-hydroxyethoxy)-3'-methoxy-5'-methyl-6-(5-methyl-1,2,4-oxadiazol-3-yl)spiro[benzofuran-2,4'-cyclohex-2-ene]-1',3-dione 16a (2S,5'R)-7-Chloro-4-hydroxy-3'-methoxy-5'-methyl-6-(5-methyl-1,2,4-oxadiazol-3-yl)spiro[benzofuran-2,4'-cyclohex-2-ene]-1',3-dione The compound of Example 7 (7b): (2S,5'R)-7-chloro-3',4-dimethoxy-5'-methyl-6-(5-methyl-1,2,4-oxadiazol-3-yl)spiro[benzofuran-2,4'-cyclohex-2-ene]-1',3-dione (2.3 g) was dissolved in a solvent mixture of toluene (20 mL) and ether (40 mL). To this, magnesium iodide (1.52 g) was added. The reaction mixture was stirred at 80° C. for 5 hours. To the reaction mixture, water was added. The reaction mixture was neutralized with 4 N hydrochloric acid and extracted with ethyl acetate. The organic layer was washed with water and saturated saline and dried over anhydrous sodium sulfate. The solvent was distilled away under reduced pressure and the resultant residue was purified by silica gel column chromatography [elution solvent: petroleum ether/ethyl acetate=1/1 (V/V)] to obtain the title compound (1.7 g (yield: 64%)) as a yellow solid.

16b (2S,5'R)-7-Chloro-4-(2-hydroxyethoxy)-3'-methoxy-5'-methyl-6-(5-methyl-1,2,4-oxadiazol-3-yl)spiro[benzofuran-2,4'-cyclohex-2-ene]-1',3-dione Palladium chloride (0.45 mg) was dissolved in water (2 mL). To this, tetrabutylammonium bromide (10.3 mg) and potassium carbonate (4.42 mg) were added. The reaction mixture was stirred at 60° C. for 15 minutes. To the mixture, the compound of Example 16 (16a): (2S,5'R)-7-chloro-4-hydroxy-3'-methoxy-5'-methyl-6-(5-methyl-1,2,4-oxadiazol-3-yl)spiro[benzofuran-2,4'-cyclohex-2-ene]-1',3-dione (50 mg) and oxirane (28.1 mg) were added. The mixture was stirred at 60° C. for 12 hours.

The reaction mixture was poured into water and extracted with dichloromethane. The organic layer was washed with water and saturated saline and dried over anhydrous sodium sulfate. The solvent was distilled off under reduced pressure. The resultant residue was purified by thin layer chromatography [developing solvent: ethyl acetate] to obtain the title compound (16 mg (yield: 29%) as a yellow solid.

In the following tables, the structural formulae of the compounds described in the Examples and physicochemical data thereof are collectively shown.

TABLE 2

| Example No. | Structural formula | Physicochemical data |
|---|---|---|
| 1(1a) | | $^1$H NMR (400 MHz, DMSO-d$_6$): δ (ppm) = 12.04 (1H, brs), 6.28 (1H, s), 5.59 (1H, s), 3.81 (3H, s), 3.63 (3H, s), 2.83-2.73 (1H, m), 2.68 (1H, dd, J = 16.6, 13.2 Hz), 2.34 (1H, dd, J = 16.6, 4.9 Hz), 0.81 (3H, d, J = 6.8 Hz). |
| 1(1b) | | $^1$H NMR (400 MHz, CDCl$_3$): δ (ppm) = 6.15 (1H, s), 5.55 (1H, s), 4.28 (2H, t, J = 4.8 Hz), 4.10-4.04 (2H, m), 3.97 (3H, s), 3.62 (3H, s), 3.04 (1H, dd, J = 16.6, 13.2 Hz), 2.89-2.80 (1H, m), 2.44 (1H, dd, J = 16.6, 4.9 Hz), 2.10 (1H, t, J = 6.4 Hz), 0.97 (3H, d, J = 6.4 Hz). MS(ESI) m/z: 383 (M + H)$^+$ |
| 2 | | $^1$H NMR (400 MHz, CDCl$_3$): δ (ppm) = 6.19 (1H, s), 5.54 (1H, s), 4.31 (2H, t, J = 4.4 Hz), 3.95 (3H, s), 3.85 (2H, t, J = 4.4 Hz), 3.61 (3H, s), 3.50 (3H, s), 3.04 (1H, dd, J = 16.6, 13.7 Hz), 2.89-2.79 (1H, m), 2.43 (1H, dd, J = 16.6, 4.4 Hz), 0.96 (3H, d, J = 6.8 Hz), MS (ESI) m/z: 397 (M + H)$^+$ |
| 3(3a) | | $^1$H NMR (400 MHz, CDCl$_3$): δ (ppm) = 6.54 (1H, s), 5.58 (1H, s), 3.99 (3H, s), 3.65 (3H, s), 2.97 (1H, dd, J = 16.6, 13.2 Hz), 2.93-2.81 (1H, m), 2.48 (1H, dd, J = 16.1, 4.4 Hz), 0.98 (3H, d, J = 6.8 Hz). |
| 3(3b) | | $^1$H NMR (400 MHz, CDCl$_3$): δ (ppm) = 7.49 (1H, d, J = 2.4 Hz), 7.12 (1H, s), 7.01 (1H, d, J = 2.4 Hz), 5.57 (1H, s), 4.02 (3H, s), 4.02 (3H, s), 3.63 (3H, s), 3.05 (1H, dd, J = 16.6, 13.3 Hz), 2.95-2.82 (1H, m), 2.46 (1H, dd, J = 16.6, 4.3 Hz), 0.99 (3H, d, J = 6.7 Hz). MS(ESI) m/z: 403 (M + H)$^+$ |
| 4 | | $^1$H NMR (400 MHz, CDCl$_3$): δ (ppm) = 7.53 (1H, d, J = 2.4 Hz), 7.14 (1H, s), 7.01 (1H, d, J = 2.4 Hz), 5.57 (1H, s), 4.29 (2H, q, J = 7.3 Hz), 4.03 (3H, s), 3.64 (3H, s), 3.05 (1H, dd, J = 16.6, 13.3 Hz), 2.94-2.83 (1H, m), 2.47 (1H, dd, J = 16.6, 4.9 Hz), 1.58 (3H, t, J = 7.3 Hz), 1.00 (3H, d, J = 6.4 Hz). MS(ESI) m/z: 417 (M + H)$^+$ |

TABLE 3

| Example No. | Structural formula | Physicochemical data |
|---|---|---|
| 5(5a) | | $^1$H NMR (400 MHz, CDCl$_3$): δ (ppm) = 7.48 (2H, s), 7.23 (1H, s), 5.59 (1H, s), 4.05 (3H, s), 3.65 (3H, s), 3.00 (1H, dd, J = 16.1, 13.2 Hz), 2.95-2.82 (1H, m), 2.50 (1H, dd, J = 16.1, 4.4 Hz), 1.00 (3H, d, J = 6.8 Hz). |
| 5(5b) | | $^1$H NMR (400 MHz, CDCl$_3$): δ (ppm) = 9.00 (1H, brd, J = 5.4 Hz), 8.59 (1H, brd, J = 5.4 Hz), 6.88 (1H, s), 5.58 (1H, s), 4.00 (3H, s), 3.64 (3H, s), 2.99 (1H, dd, J = 16.6, 13.2 Hz), 2.92-2.83 (1H, m), 2.48 (1H, dd, J = 16.6, 4.4 Hz), 2.17 (3H, s,), 0.96 (3H, d, J = 6.4 Hz). |
| 5(5c) | | $^1$H NMR (400 MHz, CDCl$_3$): δ (ppm) = 7.23 (1H, s), 5.59 (1H, s), 4.04 (3H, s), 3.65 (3H, s), 3.05-2.97 (1H, m), 2.95-2.86 (1H, m), 2.71 (3H, s), 2.53-2.45 (1H, m), 1.00 (3H, d, J = 6.9 Hz). MS(ESI) m/z: 405 (M + H)$^+$. |
| 6(6a) | | $^1$H NMR (400 MHz, CDCl$_3$): δ (ppm) = 6.96 (1H, s), 5.57 (1H, s), 5.03 (2H, brs), 4.00 (3H, s), 3.64 (3H, s), 3.00 (1H, dd, J = 16.6, 13.2 Hz), 2.93-2.83 (1H, m), 2.48 (1H, dd, J = 16.6, 4.4 Hz), 2.08 (3H, s), 0.98 (3H, d, J = 6.4 Hz). |
| 6(6b) | | $^1$H NMR (400 MHz, CDCl$_3$): δ (ppm) = 7.24 (1H, s), 5.59 (1H, s), 4.05 (3H, s), 3.65 (3H, s), 3.00 (1H, dd, J = 16.6, 13.2 Hz), 2.96-2.86 (1H, m), 2.56 (3H, s), 2.50 (1H, dd, J = 16.6, 4.4 Hz), 1.00 (3H, d, J = 6.6 Hz). MS(ESI) m/z: 405 (M + H)$^+$ |
| 7(a) | | $^1$H NMR (400 MHz, CDCl$_3$): δ (ppm) = 6.82 (1H, s), 5.58 (1H, s), 4.00 (3H, s), 3.63 (3H, s), 2.96 (1H, dd, J = 16.1, 13.2 Hz), 2.92-2.83 (1H, m), 2.49 (1H, dd, J = 16.1, 3.9 Hz), 0.97 (3H, d, J = 6.4 Hz). |

TABLE 4

| Example No. | Structural formula | Physicochemical data |
|---|---|---|
| 7(b) | | ¹H NMR (400 MHz, CDCl₃): δ (ppm) = 7.12 (1H, s), 5.57 (1H, s), 4.02 (3H, s), 3.64 (3H, s), 3.02 (1H, dd, J = 16.6, 13.2 Hz), 2.95-2.85 (1H, m), 2.73 (3H, s), 2.48 (1H, dd, J = 16.6, 4.4 Hz), 1.00 (3H, d, J = 6.6 Hz). MS(ESI) m/z: 405 (M + H)⁺ |
| 8(a) | | ¹H NMR (400 MHz, CDCl₃): δ (ppm) = 9.39 (1H, brs), 8.83 (1H, brs), 6.91 (1H, s), 5.57 (1H, s), 4.00 (3H, s), 3.64 (3H, s), 3.00 (1H, dd, J = 16.6, 13.2 Hz), 2.93-2.82 (1H, m), 2.47 (1H, dd, J = 16.6, 4.4 Hz), 2.43 (1H, brs), 1.57 (6H, s), 0.97 (3H, d, J = 6.4 Hz). |
| 8(b) | | ¹H NMR (400 MHz, CDCl₃): δ (ppm) = 7.25 (1H, s), 5.59 (1H, s), 4.05 (3H, s), 3.64 (3H, s), 3.01 (1H, dd, J = 16.1, 13.2 Hz), 2.97-2.83 (1H, m), 2.52 (1H, m), 2.49 (1H, dd, J = 16.1, 4.4 Hz), 1.81 (6H, s), 1.00 (3H, d, J = 6.4 Hz). MS(ESI) m/z: 449 (M + H)⁺ |
| 9(a) | | ¹H NMR (400 MHz, CDCl₃): δ (ppm) = 7.89 (0.3H, brs), 7.60 (0.7H, brs), 4.65-4.60 (1H, m), 4.35-4.28 (1H, m), 3.92-3.81 (3H, m), 3.55-3.46 (1H, m), 1.90-1.72 (2H, m), 1.65-1.52 (4H, m), 1.48 (2.1H, d, J = 6.8 Hz), 1.41 (0.9H, d, J = 6.8 Hz). |
| 9(b) | | ¹H NMR (400 MHz, CDCl₃): δ (ppm) = 9.71 (0.2H, d, J = 6.8 Hz), 9.18 (0.8H, d, J = 5.9 Hz), 8.94 (0.2H, d, J = 6.4 Hz), 8.90 (0.8H, d, J = 5.9 Hz), 6.93 (0.2H, s), 6.92 (0.8H, s), 5.58 (0.2H, s), 5.57 (0.8H, s), 4.81-4.76 (0.8H, m), 4.72-4.68 (0.2H, m), 4.50-4.41 (1H, m), 3.99 (3H, s), 3.97-3.90 (1H, m), 3.68-4.54 (4H, m), 3.00 (1H, dd, J = 16.2, 13.2 Hz), 2.93-2.84 (1H, m), 2.48 (1H, dd, J = 16.2, 4.4 Hz), 1.96-1.46 (9H, m), 0.98 (3H, d, J = 6.8 Hz). |

TABLE 5

| Example No. | Structural formula | Physicochemical data |
|---|---|---|
| 9(c) | | ¹H NMR (400 MHz, CDCl₃): δ (ppm) = 7.26 (1H, s), 5.58 (1H, s), 5.26 (0.8H, q, J = 6.4 Hz), 5.17 (0.2H, q, J = 6.4 Hz), 4.93-4.89 (0.2H, m), 4.85-4.80 (0.8H, m), 4.04 (3H, s), 3.97-3.90 (0.8H, m), 3.88-3.81 (0.2H, m), 3.64 (3H, s), 3.63-3.57 (0.8H, m), 3.50-3.42 (0.2H, m), 3.01 (1H, dd, J = 16.2, 13.2 Hz), 2.95-2.85 (1H, m), 2.49 (1H, dd, J = 16.2, 4.4 Hz), 1.92-1.80 (1H, m), 1.78-1.69 (5H, m), 1.68-1.50 (3H, m), 1.00 (3H, d, J = 6.4 Hz). |
| 9(d) | | ¹H NMR (400 MHz, CDCl₃): δ (ppm) = 7.24 (1H, s), 5.58 (1H, s), 5.26 (1H, quintet J = 6.4 Hz), 4.04 (3H, s), 3.64 (3H, s), 3.01 (1H, dd, J = 16.6, 13.7 Hz), 2.95-2.85 (1H, m), 2.55 (1H, brs), 2.49 (1H, dd, J = 16.6, 4.4 Hz), 1.78 (3H, d, J = 6.4 Hz), 1.00 (3H, d, J = 6.8 Hz). MS(ESI) m/z: 435 (M + H)⁺ |
| 10(a) | | ¹H NMR (400 MHz, CDCl₃): δ (ppm) = 7.89 (0.3H, brs), 7.60 (0.7H, brs), 4.67-4.60 (1H, m), 4.36-4.27 (1H, m), 3.96-3.78 (3H, m), 3.57-3.46 (1H, m), 1.91-1.72 (2H, m), 1.65-1.52 (4H, m), 1.48 (2.1H, d, J = 6.8 Hz), 1.42 (0.9H, d, J = 6.8 Hz). |
| 10(b) | | ¹H NMR (400 MHz, CDCl₃): δ (ppm) = 9.72 (0.3H, d, J = 6.4 Hz), 9.19 (0.7H, d, J = 6.4 Hz), 9.00 (0.3H, d, J = 6.4 Hz), 8.96 (0.7H, d, J = 6.4 Hz), 6.93 (0.3H, s), 6.92 (0.7H, s), 5.57 (1H, s), 4.83-4.76 (0.7H, m), 4.74-4.67 (0.3H, m), 4.52-4.40 (1H, m), 4.07-3.88 (4H, m), 3.71-3.53 (4H, m), 3.06-2.82 (2H, m), 2.48 (1H, dd, J = 16.6, 4.4 Hz), 1.98-1.45 (9H, m), 0.97 (3H, d, J = 6.4 Hz). |
| 10(c) | | ¹H NMR (400 MHz, CDCl₃): δ (ppm)= 7.27 (1H, s), 5.58 (1H, s), 5.30 (0.7H, q, J = 6.8 Hz), 5.16 (0.3H, q, J = 6.8 Hz), 4.93-4.89 (0.3H, m), 4.85-4.80 (0.7H, m), 4.04 (3H, s), 3.97-3.90 (0.7H, m), 3.89-3.81 (0.3H, m), 3.64 (3H, s), 3.63-3.56 (0.7H, m), 3.50-3.41 (0.3H, m), 3.05-2.85 (2H, m), 2.53-2.45 (1H, m), 1.93-1.46 (9H, m), 0.99 (3H, d, J = 6.8 Hz). |

TABLE 6

| Example No. | Structural formula | Physicochemical data |
| --- | --- | --- |
| 10(d) | | $^1$H NMR (400 MHz, CDCl$_3$): δ (ppm) = 7.24 (1H, s), 5.58 (1H, s), 5.26 (1H, quintet J = 6.8 Hz), 4.04 (3H, s), 3.64 (3H, s), 3.01 (1H, dd, J = 16.2, 13.2 Hz), 2.95-2.85 (1H, m), 2.56 (1H, brs), 2.49 (1H, dd, J = 16.6, 4.4 Hz), 1.78 (3H, d, J = 6.8 Hz), 1.00 (3H, d, J = 6.8 Hz). MS(ESI) m/z: 435 (M + H)$^+$ |
| 11(a) | | $^1$H NMR (400 MHz, CDCl$_3$): δ (ppm) = 7.28 (1H, s), 5.61 (1H, s), 4.04 (1H, s), 3.68 (3H, s), 3.05-2.87 (2H, m), 2.59-2.52 (1H, m), 1.80 (6H, s), 1.02 (3H, d, J = 6.4 Hz). |
| 11(b) | | $^1$H NMR (400 MHz, CDCl$_3$): δ (ppm) = 7.22 (1H, s), 5.57 (1H, s), 4.31-4.23 (2H, m), 3.64 (3H, s), 3.02 (1H, dd, J = 16.6, 13.7 Hz), 2.95-2.85 (1H, m), 2.56-2.42 (2H, m), 1.81 (6H, s), 1.54 (3H, t, J = 6.8 Hz), 1.00 (3H, d, J = 6.4 Hz). MS(ESI) m/z: 463 (M + H)$^+$ |
| 12 | | $^1$H NMR (400 MHz, CDCl$_3$): δ (ppm = 7.22 (1H, s), 5.57 (1H, s), 5.31-5.21 (1H, m), 4.32-4.22 (2H, m), 3.64 (3H, s), 3.03 (1H, dd, J = 16.6, 13.2 Hz), 2.96-2.85 (1H, m), 2.52-2.44 (2H, m), 1.78 (3H, d, J = 6.4 Hz), 1.54 (3H, t, J = 6.8 Hz), 1.00 (3H, d, J = 6.4 Hz). MS(ESI) m/z: 449 (M + H)$^+$ |
| 13(13a) | | $^1$H NMR (400 MHz, CDCl$_3$) δ (ppm) = 4.93-4.86 (1H, m), 4.65 (1H, q, J = 6.8 Hz), 3.82-3.72 (1H, m), 3.60-3.52 (1H, m), 1.90-1.71 (2H, m), 1.69-1.49 (7H, m).<br>$^1$H NMR (400 MHz, CDCl$_3$): δ (ppm) = 4.81-4.77 (1H, m), 4.39 (1H, q, J = 6.8 Hz), 3.97 (1H, td, J = 11.7, 2.9 Hz), 3.67-3.60 (1H, m), 1.90-1.52 (9H, m). |

TABLE 7

| Example No. | Structural formula | Physicochemical data |
|---|---|---|
| 13(13b) | (structure) | $^1$H NMR (400 MHz, CDCl$_3$): δ (ppm) = 7.70 (1H, brs), 4.70 (2H, brs), 4.63-4.58 (1H, m), 4.36 (1H, q, J = 6.8 Hz), 3.93-3.83 (1H, m), 3.56-3.48 (1H, m), 1.90-1.78 (1H, m), 1.75-1.66 (1H, m), 1.63-1.49 (4H, m), 1.44 (3H, d, J = 6.8 Hz). |
| 13(13c) | (structure) | $^1$H NMR (400 MHz, CDCl$_3$): δ (ppm) = 6.97 (1H, s), 5.57 (1H, s), 5.21 (2H, brs), 4.78-4.61 (2H, m), 4.00 (3H, s), 3.94-3.85 (1H, m), 3.63 (3H, s), 3.59-3.51 (1H, m), 3.00 (1H, dd, J = 16.6, 13.7 Hz), 2.93-2.82 (1H, m), 2.48 (1H, dd, J = 16.6, 4.4 Hz), 1.90-1.79 (1H, m), 1.78-1.69 (1H, m), 1.63-1.49 (7H, m), 0.98 (3H, d, J = 6.8 Hz). |
| 13(13d) | (structure) | $^1$H NMR (400 MHz, CDCl$_3$): δ (ppm) = 7.27 (1H, s), 5.58 (1H, s), 5.23 (1H, q, J = 6.8 Hz), 4.79-4.70 (1H, m), 4.05 (3H, s), 3.99-3.92 (1H, m), 3.63 (3H, s), 3.62-3.56 (1H, m), 3.00 (1H, dd, J = 16.6, 13.7 Hz), 2.95-2.85 (1H, m), 2.49 (1H, dd, J = 16.6, 4.4 Hz), 1.94-1.83 (1H, m), 1.78-1.50 (8H, m), 0.99 (3H, d, J = 6.8 Hz). |
| 13(13e) | (structure) | $^1$H NMR (400 MHz, CDCl$_3$): δ (ppm) = 7.25 (1H, s), 5.58 (1H, s), 5.17 (1H, quintet, J = 6.8 Hz), 4.06 (3H, s), 3.64 (3H, s), 3.00 (1H, dd, J = 16.6, 13.2 Hz), 2.96-2.85 (1H, m), 2.50 (1H, dd, J = 16.6, 4.4 Hz), 2.48-2.43 (1H, m), 1.73 (3H, d, J = 6.8 Hz), 1.00 (3H, d, J = 6.4 Hz). MS(ESI) m/z: 435 (M + H)$^+$ |
| 14(14a) | (structure) | $^1$H NMR (400 MHz, CDCl$_3$): δ (ppm) = 7.76 (1H, brs), 6.19 (1H, s), 5.57 (1H, s), 3.98 (3H, s), 3.66 (3H, s), 3.00-2.82 (2H, m), 2.49 (1H, dd, J = 16.6, 4.4 Hz), 0.99 (3H, d, J = 6.4 Hz). |

TABLE 7-continued

| Example No. | Structural formula | Physicochemical data |
|---|---|---|
| 14(14b) | | $^1$H NMR (400 MHz, CDCl$_3$): δ (ppm) = 6.26 (1H, s), 5.54 (1H, s), 4.75-4.69 (1H, m), 4.40-4.29 (2H, m), 4.15-4.08 (1H, m), 4.00 (3H, s), 3.96-3.85 (2H, m), 3.62 (3H, s), 3.57-3.50 (1H, m), 3.03 (1H, dd, J = 16.6, 13.2 Hz), 2.89-2.79 (1H, m), 2.46-2.39 (1H, m), 1.88-1.68 (2H, m), 1.62-1.45 (4H, m), 0.96 (3H, d, J = 6.8 Hz). |

TABLE 8

| Example No. | Structural formula | Physicochemical data |
|---|---|---|
| 14(14c) | | $^1$H NMR (400 MHz, CDCl$_3$): δ (ppm) = 6.30 (1H, s), 5.54 (1H, s), 4.78-4.71 (1H, m), 4.30-4.21 (2H, m), 4.12-4.04 (1H, m), 3.95-3.84 (2H, m), 3.63 (3H, s), 3.57-3.50 (1H, m), 3.04 (1H, dd, J = 16.6, 13.2 Hz), 2.88-2.77 (1H, m), 2.46-2.39 (1H, m), 1.85-1.47 (6H, m), 0.97 (3H, d, J = 6.8 Hz). |
| 14(14d) | | $^1$H NMR (400 MHz, CDCl$_3$): δ (ppm) = 6.67 (1H, s), 5.57 (1H, s), 4.75-4.70 (1H, m), 4.37-4.28 (2H, m), 4.15-4.07 (1H, m), 3.93-3.84 (2H, m), 3.65 (3H, s), 3.57-3.51 (1H, m), 3.01-2.93 (1H, m), 2.92-2.81 (1H, m), 2.52-2.44 (1H, m), 1.84-1.68 (2H, m), 1.65-1.46 (4H, m), 0.98 (3H, d, J = 6.8 Hz). |

TABLE 8-continued

| Example No. | Structural formula | Physicochemical data |
|---|---|---|
| 14(14e) | | $^1$H NMR (400 MHz, CDCl$_3$): δ (ppm) = 7.47 (2H, s), 7.32 (1H, s), 5.58 (1H, s), 4.76-4.72 (1H, m), 4.44-4.36 (2H, m), 4.17-4.07 (1H, m), 3.96-3.84 (2H, m), 3.65 (3H, s), 3.57-3.49 (1H, m), 3.04-2.96 (1H, m), 2.95-2.86 (1H, m), 2.52-2.44 (1H, m), 1.83-1.67 (2H, m), 1.64-1.44 (4H, m), 0.99 (3H, d, J = 6.8 Hz). |
| 14(14f) | | $^1$H NMR (400 MHz, CDCl$_3$): δ (ppm) = 8.97-8.86 (1H, m), 8.45-8.32 (1H, m), 6.96 (1H, s), 5.56 (1H, s), 4.77-4.70 (1H, m), 4.40-4.29 (2H, m), 4.14-4.05 (1H, m), 3.94-3.84 (2H, m), 3.64 (3H, s), 3.57-3.50 (1H, m), 3.00 (1H, dd, J = 16.1, 13.6 Hz), 2.93-2.82 (1H, m), 2.47 (1H, dd, J = 16.6, 3.9 Hz), 2.16 (3H, s), 1.87-1.67 (2H, m), 1.64-1.46 (4H, m), 0.97 (3H, d, J = 6.8 Hz). |

TABLE 9

| Example No. | Structural formula | Physicochemica data |
|---|---|---|
| 14(14g) | | $^1$H NMR (400 MHz, CDCl$_3$): δ (ppm) = 7.29 (1H, s), 5.57 (1H, s), 4.78-4.72 (1H, m), 4.43-4.33 (2H, m) 4.16-4.08 (1H, m), 3.96-3.85 (2H, m), 3.64 (3H, s), 3.58-3.51 (1H, m), 3.01 (1H, dd, J = 16.1, 13.2 Hz), 2.95-2.85 (1H, m), 2.70 (3H, s), 2.52-2.44 (1H, m), 1.85-1.68 (2H, m), 1.64-1.47 (4H, m), 0.99 (3H, d, J = 6.4 Hz). |

TABLE 9-continued

| Example No. | Structural formula | Physicochemical data |
|---|---|---|
| 14(14h) | | $^1$H NMR (400 MHz, CDCl$_3$): δ (ppm) = 7.25 (1H, s), 5.58 (1H, s), 4.33-4.23 (2H, m), 4.10-3.96 (2H, m), 3.65 (3H, s), 3.04-2.85 (2H, m), 2.71 (3H, s), 2.60-2.46 (2H, m), 1.00 (3H, d, J = 6.8 Hz). MS(ESI) m/z: 435 (M + H)$^+$ |
| 15(15a) | | $^1$H NMR (400 MHz, CDCl$_3$): δ (ppm) = 7.04 (1H, s), 5.56 (1H, s), 4.78-4.72 (1H, m), 4.40-4.29 (2H, m), 4.14-4.06 (1H, m), 3.93-3.84 (2H, m), 3.64 (3H, s), 3.57-3.50 (1H, m), 3.00 (1H, dd, J = 16.6, 13.2 Hz), 2.93-2.82 (1H, m), 2.47 (1H, dd, J = 16.6, 3.2 Hz), 2.08 (3H, s), 1.85-1.67 (2H, m), 1.64-1.47 (4H, m), 0.97 (3H, d, J = 6.4 Hz). |
| 15(15b) | | $^1$H NMR (400 MHz, CDCl$_3$): δ (ppm) = 7.33 (1H, s), 5.57 (1H, s), 4.78-4.72 (1H, m), 4.45-4.34 (2H, m), 4.16-4.08 (1H, m), 3.96-3.83 (2H, m), 3.64 (3H, s), 3.58-3.51 (1H, m), 3.00 (1H, dd, J = 16.1, 13.2 Hz), 2.95-2.86 (1H, m), 2.54 (3H, s), 2.48 (1H, dd, J = 16.1, 3.2 Hz), 1.85-1.68 (2H, m), 1.64-1.47 (4H, m), 0.99 (3H, d, J = 6.4 Hz). |
| 15(15c) | | $^1$H NMR (400 MHz, CDCl$_3$): δ (ppm) = 7.25 (1H, s), 5.58 (1H, s), 4.33-4.25 (2H, m), 4.09-3.98 (2H, m), 3.65 (3H, s), 2.99 (1H, dd, J = 16.1, 13.2 Hz), 2.96-2.87 (1H, m), 2.55 (3H, s), 2.54 (1H, d, J = 6.4 Hz), 2.50 (1H, dd, J = 16.1, 3.9 Hz), 1.00 (3H, d, J = 6.4 Hz). MS(ESI) m/z: 435 (M + H)$^+$ |

TABLE 10

| Example No. | Structural formula | Physicochemical data |
|---|---|---|
| 16(a) | 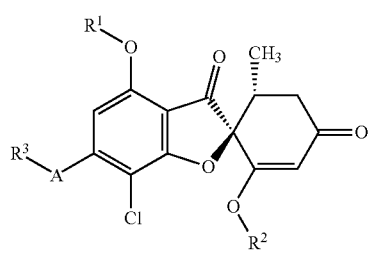 | $^1$H NMR (400 MHz, CDCl$_3$): δ (ppm) = 7.72 (1H, brs), 7.16 (1H, s), 5.60 (1H, s), 3.68 (3H, s), 3.10-2.85 (2H, m), 2.72 (3H, s), 2.59-2.43 (1H, m), 1.01 (3H, d, J = 6.4 Hz). |
| 16(b) | 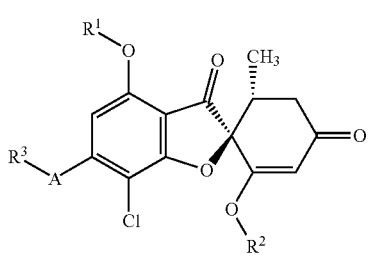 | $^1$H NMR (400 MHz, CDCl$_3$): δ (ppm) = 7.15 (1H, s), 5.58 (1H, s), 4.38-4.23 (2H, m), 4.15-3.95 (2H, m), 3.66 (3H, s), 3.08-2.85 (2H, m), 2.74 (3H, s), 2.49 (1H, dd, J = 16.1, 3.9 Hz), 1.00 (3H, d, J = 6.4 Hz). MS(ESI) m/z: 435 (M + H)$^+$ |

The invention claimed is:

1. A compound of general formula (1) or a pharmacologically acceptable salt thereof:

(1)

[Structural formula of compound (1)]

Wherein the symbols in the formula are defined below:

R$^1$: a C1-C6 alkyl group,

R$^2$: a C1-C6 alkyl group,

A: a 5-membered aromatic heterocycle having 1-4 atoms selected from the group consisting of a nitrogen atom, an oxygen atom and a sulfur atom, and R$^3$: a C1-C6 alkyl group.

2. The compound or a pharmacologically acceptable salt thereof according to claim 1, wherein R$^1$ is a methyl group or an ethyl group.

3. The compound or a pharmacologically acceptable salt thereof according to claim 1, wherein R$^2$ is a methyl group.

4. The compound or a pharmacologically acceptable salt thereof according to claim 1, wherein A is a 5-membered aromatic heterocycle having 1-4 atoms selected from the group consisting of a nitrogen atom, an oxygen atom and a sulfur atom; and R$^3$ is a methyl group or an ethyl group.

5. The compound or a pharmacologically acceptable salt thereof according to claim 1, wherein A is a 5-membered aromatic heterocycle selected from the following group:

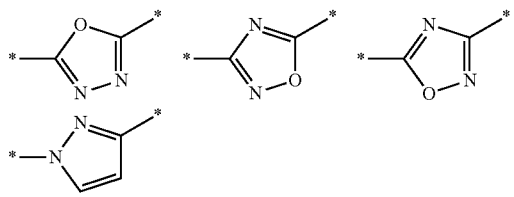

wherein * represents a bond.

6. A compound of general formula (1) or a pharmacologically acceptable salt thereof:

(1)

[Structural formula of compound (1)]

wherein the symbols in the formula are defined below:

R$^1$: a methyl group or an ethyl group,

R$^2$: a methyl group,

A: a 5-membered aromatic heterocycle selected from the following group:

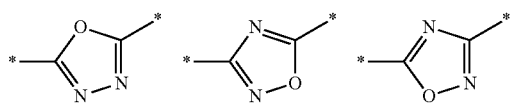

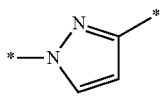

wherein * represents a bond, and

R³: a methyl group or an ethyl group.

7. A pharmaceutical composition containing a compound or a pharmacologically acceptable salt thereof according to claim 1, as an active ingredient.

8. A method of treating an inflammatory disease in a subject in need thereof, comprising administering to the subject an effective amount of the pharmaceutical composition according to claim 7.

9. The method according to claim 8, wherein the inflammatory disease is a disease selected from the group consisting of rheumatoid arthritis, systemic lupus erythematosus, scleroderma, bronchial asthma, asthmatic bronchitis, diffuse interstitial pneumonia, chronic obstructive pulmonary disease, ulcerative colitis, Crohn's disease, acute hepatitis, chronic hepatitis, fulminant hepatitis, autoimmune hepatitis, primary biliary cirrhosis, primary sclerosing cholangitis, alcoholic hepatitis, non-alcoholic steatohepatitis, cirrhosis, peripheral neuritis, ankylosing spondylitis, eczema (acute, subacute, chronic), contact dermatitis, sunlight (ultraviolet light) dermatitis, radiation dermatitis, atopic dermatitis, seborrheic dermatitis, psoriasis vulgaris, arthropathic psoriasis, psoriatic erythroderma, pustular psoriasis, lichen planus, erythema, rosacea, urticaria, alopecia areata, pemphigus, erythroderma, acne vulgaris, pressure sore, wound, burn, conjunctivitis, keratitis, scleritis, acute/chronic otitis media, perennial allergic rhinitis, hay fever, sinusitis, laryngitis, esophagitis, refractory stomatitis, glossitis, acute/chronic salivary gland inflammation, angular cheilitis, cheilitis Behcet's disease, multiple sclerosis, Type I diabetes, Type II diabetes, atherosclerosis, pancreatitis and chronic heart failure.

10. The method according to claim 8, wherein the inflammatory disease is a disease selected from the group consisting of rheumatoid arthritis, systemic lupus erythematosus, bronchial asthma, acute hepatitis, autoimmune hepatitis, primary biliary cirrhosis, primary sclerosing cholangitis, alcoholic hepatitis, nonalcoholic steatohepatitis, ankylosing spondylitis, contact dermatitis, sunlight (UV) dermatitis, atopic dermatitis, seborrheic dermatitis, psoriasis vulgaris, arthropathic psoriasis, psoriatic erythroderma, pustular psoriasis, lichen plant's, erythema, rosacea, alopecia areata, pemphigus, erythroderma, acne vulgaris, pressure sore, wound, burn, sinusitis, laryngitis, esophagitis, refractory stomatitis, glossitis, acute chronic salivary gland inflammation, angular cheilitis, cheilitis and Behcet's disease.

11. The method according to claim 8, wherein the inflammatory disease is a disease selected from the group consisting of rheumatoid arthritis, systemic lupus erythematosus, autoimmune hepatitis, alcoholic hepatitis, nonalcoholic steatohepatitis, ankylosing spondylitis, atopic dermatitis, psoriasis vulgaris, arthropathic psoriasis, psoriatic erythroderma, pustular psoriasis, lichen planus, pressure sore, wound, refractory stomatitis, glossitis and Behcet's disease.

12. A method of treating an inflammatory disease in a subject in need thereof, comprising administering to the subject an effective amount of the compound or a pharmacologically acceptable salt thereof according to claim 1.

13. A TNT-α inhibitor containing a compound or a pharmacologically acceptable salt thereof according to claim 1, as an active ingredient.

* * * * *

UNITED STATES PATENT AND TRADEMARK OFFICE
CERTIFICATE OF CORRECTION

| | |
|---|---|
| PATENT NO. | : 11,472,784 B2 |
| APPLICATION NO. | : 17/212373 |
| DATED | : October 18, 2022 |
| INVENTOR(S) | : Saito et al. |

It is certified that error appears in the above-identified patent and that said Letters Patent is hereby corrected as shown below:

In the Specification

Column 4, Line 24: Please correct "general formula or" to read --general formula (1) or--

Column 8, Line 23: Please correct "a hydroxyethyl group" to read --a 2-hydroxyethyl group--

Column 8, Line 29: Please correct "C7-C6" to read --C1-C6--

Column 13, Line 43: Please correct "$B^+$" to read --B*--

Column 13, Line 64: Please correct "$R^3$-A-$B^+$" to read --$R^3$-A-B*--

Column 14, Line 6: Please correct "(DEN)" to read --(DBN)--

Column 18, Lines 21-22: Please correct "0-(7-azabenzotriazol-1-yl)" to read --O-(7-azabenzotriazol-1-yl)--

Column 19, Line 40: Please correct "$R^{1''}$ or $R^{3'''}$" to read --$R^{1'}$ or $R^{3'}$--

Column 20, Line 15: Please correct "$R^{1''}$ or $R^{3'''}$" to read --$R^{1'}$ or $R^{3'}$--

Column 20, Line 40: Please correct "(TRAF)" to read --(TBAF)--

Column 23, Line 9: Please correct "(I)" to read --(%)--

Column 24, Line 15: Please correct "-1',3-3-dione" to read -- -1',3-dione--

Column 24, Line 21: Please correct "(0.0738))" to read --(0.0738 g)--

Signed and Sealed this
Twenty-first Day of February, 2023

*Katherine Kelly Vidal*

Katherine Kelly Vidal
*Director of the United States Patent and Trademark Office*

CERTIFICATE OF CORRECTION (continued)
U.S. Pat. No. 11,472,784 B2

Column 24, Line 41: Please correct "(136 rag)" to read --(136 mg)--

Column 25, Line 9: Please correct "(yield: 852))" to read --(yield: 85%))--

Column 25, Line 25: Please correct "(0.0403))" to read --(0.0403 g)--

Column 26, Line 17: Please correct "(0.477))" to read --(0.477 g)--

Column 26, Line 41: Please correct "(3.5 g)" to read --(35 g)--

Column 27, Line 40: Please correct "methyl-1-1,2,4-" to read --methyl-1,2,4- --

Column 27, Line 62: Please correct "-7-Chloro-3'," to read -- -7-Chloro-1',--

Column 28, Lines 24-25: Please correct "(0.19 mm)" to read --(0.19 mL)--

Column 29, Line 24: Please correct "(0.254))" to read --(0.254 g)--

Column 29, Line 37: Please correct "-hyroxyethyl" to read -- -hydroxyethyl--

Column 29, Line 46: Please correct "Ora." to read --Org.--

Column 29, Line 47: Please correct "1086-1093" to read --1088-1093--

Column 31, Line 13: Please correct "7068-2073) (1.6))" to read --2068-2073) (1.6 g)--

Column 33, Line 18: Please correct "(0.191))" to read --(0.191 g)--

Column 33, Line 59: Please correct "(0.485 were" to read --(0.485 mL) were--

Column 34, Line 53: Please correct "-3,3T-dioxo-" to read -- -3,3'-dioxo- --

Column 37, Line 16: Please correct "1-methoxy-" to read --1'-methoxy- --

In the Claims

Column 62, Line 14, Claim 10: Please correct "lichen plant's" to read --lichen planus--